US008697411B2

(12) United States Patent
Clausen et al.

(10) Patent No.: US 8,697,411 B2
(45) Date of Patent: Apr. 15, 2014

(54) STREPTOMYCES GRISEOPLANUS COMPRISING AN α-GALACTOSIDASE FOR REMOVING IMMUNODOMINANT α-GALACTOSE MONOSACCHARIDES FROM BLOOD GROUP B OR AB REACTIVE CELLS

(75) Inventors: Henrik Clausen, Holte (DK); Humberto de la Vega, Salem, MA (US); Cheryl Hill, North Andover, MA (US); Qiyong Peter Liu, Newton, MA (US)

(73) Assignee: Velico Medical, Inc., Beverly, MA (US)

( * ) Notice: Subject to any disclaimer, the term of this patent is extended or adjusted under 35 U.S.C. 154(b) by 291 days.

(21) Appl. No.: 13/205,588

(22) Filed: Aug. 8, 2011

(65) Prior Publication Data

US 2012/0202273 A1 Aug. 9, 2012

Related U.S. Application Data

(60) Continuation of application No. 12/789,946, filed on May 28, 2010, now Pat. No. 7,993,896, which is a division of application No. 10/251,271, filed on Sep. 20, 2002, now Pat. No. 7,767,415.

(60) Provisional application No. 60/361,769, filed on Mar. 5, 2002, provisional application No. 60/324,970, filed on Sep. 25, 2001.

(51) Int. Cl.
*C12N 9/24* (2006.01)

(52) U.S. Cl.
USPC ............................................... 435/200

(58) Field of Classification Search
None
See application file for complete search history.

(56) References Cited

U.S. PATENT DOCUMENTS

| 4,209,509 | A | 6/1980 | Inouye et al. |
| 4,330,619 | A | 5/1982 | Goldstein |
| 4,427,777 | A | 1/1984 | Goldstein |
| 4,609,627 | A | 9/1986 | Goldstein |
| 5,082,778 | A | 1/1992 | Overbeeke et al. |
| 5,478,738 | A | 12/1995 | Goldstein et al. |
| 5,491,075 | A | 2/1996 | Desnick et al. |
| 5,606,042 | A | 2/1997 | Smith et al. |
| 5,633,130 | A | 5/1997 | Smith et al. |
| 5,731,426 | A | 3/1998 | Smith et al. |
| 5,925,541 | A | 7/1999 | Goldstein et al. |
| 6,184,017 | B1 | 2/2001 | Smith et al. |
| 6,228,631 | B1 | 5/2001 | Zhu et al. |
| 6,329,191 | B1 | 12/2001 | Ivy et al. |
| 6,423,525 | B2 | 7/2002 | Landry |
| 6,458,573 | B1 | 10/2002 | Landry |
| 7,767,415 | B2 | 8/2010 | Clausen et al. |
| 2001/0006772 | A1 | 7/2001 | Goldstein et al. |

FOREIGN PATENT DOCUMENTS

| WO | WO 94/09123 | 4/1994 |
| WO | WO 94/12628 | 6/1994 |
| WO | WO 94/23869 | 10/1994 |
| WO | WO 96/23869 | 8/1996 |
| WO | WO 96/40714 | 12/1996 |
| WO | WO 99/23210 | 5/1999 |

OTHER PUBLICATIONS

Williams, S.T. et al. "Numerical Classification of Streptomyces and Related Genera", Journal of General Microbiology, 1983, vol. 129, pp. 1743-1813 (see pp. 1754, 1795).*
Boeck, L.D. et al. "Production of Anticapsin by Streptomyces griseoplanus", Applied Microbiology, 1971, vol. 21, No. 6, pp. 1075-1079 (see Abstract).*
Clausen, et al. (1985). Proc Natl Acad Sci USA 82: 1199-1203.
Clausen, et al. (1986). J Biol Chem 261(3): 1380-1387.
Clausen, et al. (1986). Biochem 25(22): 7075-7085.
Clausen, et al. (1987). J Biol Chem 262(29): 14228-14234.
Clausen and Hakmomori (1989). Vox Sang 56(1): 1-20.
Courtois and Petek (1996). Methods Enzymol 3: 565-571.
Davis, et al. (1996). Biochem & Molecular Biolo Int'l 39(3): 471-485.
Dean and Sweeley (1979). J Biol Chem 254(20): 10001-10005.
Falk, et al. (1991). Arch Biochem Biophys 290(2): 312-319.
Goldstein (1984). Prog Clin Biol Res 165: 139-157.
Hata, et al. (1992). Biochem Int 28 (1): 77-86.
Henrissat, et al. (1998). Biochem Soc Trans 26(2): 153-156.
Hoskins, et al. (1997). J Bio Chem 272(12): 7932-7939.
Hoskins, et al. (2001). Transfusion 41: 908-916.
Hsieh, et al. (2000). IUBMB Life 50(2): 91-97.
Izumi, et al. (1992). Biochem Biophys Acta 1116(1): 72-74.
Kruskall, et al. (2000). Transfusion 40: 1290-1298.
Levy and Animoff (1980). J Biol Chem 255(24): 11737-11742.
Rye and Withers (2000). Curr Opin Chem Biol 4: 573-580.

(Continued)

*Primary Examiner* — Sheridan Swope
(74) *Attorney, Agent, or Firm* — Antoinette G. Giugliano; AGG Intellectual Property Law

(57) ABSTRACT

This invention relates to enzymatic removal of type A and B antigens from blood group A, B, and AB reactive cells in blood products, and thereby converting these to non-A and non-B reactive cells. The invention further relates to using unique α-N-acetylgalactosaminidases and α-galactosidases with superior kinetic properties for removing the immunodominant monosaccharides of the blood group A and B antigens and improved performance in enzymatic conversion of red blood cells. The preferred unique α-N-acetylgalactosaminidases and α-galactosidases exhibit the following characteristics: (i) exclusive, preferred or no less than 10% substrate specificity for the type A and B branched polysaccharide structures relative to measurable activity with simple mono- and disaccharide structures and aglycon derivatives hereof; (ii) optimal performance at neutral pH with blood group oligosaccharides and in enzymatic conversion of cells; and (iii) a favorable kinetic constant $K_m$ with mono- and oligosaccharide substrates. The conversion methods of the invention use significantly lower amounts of recombinant glycosidase enzymes than previous and result in complete sero-conversion of all blood group A and B red cells.

4 Claims, 19 Drawing Sheets

(56) References Cited

OTHER PUBLICATIONS

Tsuji, et al. (1989). Biochem Biophys Res Comm 163(3): 1498-1504.
Vosnidou (1998). Biochem Mol Biol Int 46(1): 175-186.
Wang, et al. (1990). J Biol Chem 265(35) : 21859-21866.
Zhu, et al. (1995). Arch Biochem Biophys 324(1) : 65-70.
Zhu, et al. (1996). Arch Biochem Biophys 327(2) : 324-329.
Zhu, et al. (1996). Protein Expression and Purification 8: 456-462.
Bakunina, et al. (1998). Biochem (Moscow) 63: 1209-1215.
Harpaz, et al. (1977). Eur J Biochem 77: 419-429.
Hobbs, et al. (1995). Biomed & Pharmacother 5 : 144-250.
International Search Report for PCT/US02/30403, Mailed Aug. 8, 2003.
Larson, et al.; Degradation of human intestinal glycoshpingolipids by extracellular glycosidases from mucin-degrading bacteria of the human fecal flora; Journal of Biological Chemistry; vol. 263, No. 22, 1998, pp. 10790-10798.
Hoskins, et al.; Blood group A immunodeterminants on human red cells differ in biologic activity and sensitivity to alpha-N-acetylgalactosaminidase; Transfusion (Bethesda), vol. 35, No. 10, 1995, pp. 813-821.
Phillips, et al.; Characterization of *Gallus domesticus* alpha-N-acetyl-galactosaminidase blood group A2 activity; Artificial Cells, Blood Substitutes, and Immobilization Biotechnology; Marcel Dekker Inc., US, vol. 23, No. 1, 1995, pp. 63-79.
O'Neill, R.A.; Enzymatic release of oligosaccharides from glycoproteins for chromatographic and electrophoretic analysis; Journal of Chromatography A, Elsevier, Amsterdam. NL, vol. 720, No. 1, Jan. 12, 1996, pp. 201-215.
Ito, et al.; Histochemical localization and analysis of blood group-related antigens in human pancreas using immunostaining with monoclonal antibodies and exoglycosidase digestion; Journal of Histochemistry and Cytochemistry, vol. 38, No. 9, 1990, pp. 1331-1340.
Sarode, et al.; Role of A and B blood group antigens in the expression of adhesive activity of von Willebrand factor; British Journal of Haematology, vol. 109, No. 4, Jun. 2000, pp. 857-864.
Goldstein, et al.; Further evidence for the presence of a antigen on group B erythrocytes through the use of specific exoglycosidases; Vox Sanguinis, vol. 57, No. 2, 1989, pp. 142-146.
Kruskall, et al.; Transfusion to blood group A and O patients of group B RBCs that have been enzymatically converted to group O; Transfusion (Bethesda), vol. 40, No. 11, Nov. 2000, pp. 1290-1298.
Schmidt et al.; "The Determination of Antibody to Group a Streptococcal polysaccharide in Human Sera by Hemagglutination;" J. Exp. Med.; 1965; vol. 121; pp. 793-806.
Oishi & Aida, "Some Kinetic Properties of .alpha.-D-Galactosidase from Streptomyces 9917S.sub.2", Agr. Biol. Chem., 1976, vol. 40, pp. 57-65.
USPTO in house search of the ATCC bacterial database for "PTA-4077"; Mar. 3, 2008.
Kondoh, et al., "Cloning and Expression of the Gene Encoding Streptomyces coelicolor A3(2) Alpha-Galactosidase Belonging to Family 36", Biotechnol Lett., May 2005, vol. 25(9), pp. 641-647.
Leder, et al., "Alpha-Galactosidase of *Bifidobacterium adolescentis* DSM 20083", Curr Microbiol., Feb. 1999, vol. 38(2), pp. 101-106.
Ito et al., "Estimation and comparison of the contents of blood group B antigens in selected human tissues by microphotometric quantification of *Griffonia simplicifolia* agglutinin I-B4 staining", Histol Histopathol. 1997, vol. 12, pp. 415-424.
Chien et al., "The conversion of group B red blood cells into group O by an alpha-D-galactosidase from taro (*Colocasia esculenta*)", Carbohydr Res., 1991, vol. 18, pp. 191-200.
Davis et al., "Cloning, sequence, and expression of a blood group B active recombinant alpha-D-galactosidase from pinto bean (*Phaseolus vulgaris*)", Biochem Mol Biol Int. 1997, vol. 42, pp. 453-467.
Guyton and Hall, "Normal hydrogen ion concentran and pH of body fluids", In: Textbook of Medical Physiology W.B. Saunders Col, Philadelphia, PA, 1996, p. 386.
Willard et al., J. Exp. Med., 1965, 121: 793-806.
Extended European Search Report—(EP10182388.8), Date of Completion of the Search Feb. 8, 2011.
Lopez-Fernandez, et al., "Application of the Affinity Binding of Xylanases to Oat-spelt Xylan in the Purification of Endoxylanase CM-2 from *Streptomyces chattanoogensis* CECT 3336", Applied Microbiology and Biotechnology, Springer Verlag, Berlin, DE, 1998, vol. 50, pp. 284-287.
Boeck, et al., "Production of Anticapsin by *Streptomyces griseoplanus*", Applied Microbiology, 1971, vol. 21, pp. 1075-1079.
Williams, et al., "Numerical Classification of *Streptomyces* and Related Genera", Journal of General Microbiology, 1983, vol. 129, pp. 1743-1813.
Oishi, et al., "Conversion of Human Blood Group B and AB Red Blood Cells to Group O and A Cells by Streptomyces Enzyme", Agr. Biol. Chem., 40(1): 67-71 (1976).
Examination Report—(AU2008203095) Date of Mailing Mar. 16, 2011.

* cited by examiner

Activity of recombinant Coffee bean α-galactosidase with Galα-pNP at different pH.

Activity of recombinant Coffee bean α-galactosidase with the blood group B tetrasaccharide AMC substrate at different pH Activity of recombinant Coffee bean α-galactosidase with the Galili pentasaccharide AMC substrate at different pH HPTLC analysis of five selected Streptomycete α-galactosidase activities with the B tetrasaccharide AMC substrate.

HPTLC analysis of five selected Streptomycete α–galactosidase activities with Galα-pNP substrate.

HPTLC analysis of five selected Streptomycete α-*N*-acetylgalactosaminidase activities with the blood group A tetrasaccharide-AMC (Panel A) and A heptasaccharide-AMC (Panel B) substrates.

Analysis of Streptomycete #2357 α-galactosidase enzyme separated by S12 chromatography.

SDS-NuPAGE of pooled fractions from S12 chromatography of enzyme activity purified from #2357.

HPTLC analysis of substrate specificities of recombinant Coffee bean
α-galactosidase and purified α-galactosidase from #2357.

Activity of purified α-galactosidase from #2357 with the blood group B tetrasaccharide AMC substrate at different pH

A.

B.

Analysis of Streptomycete #2357 α-galactosidase enzyme spiked with BSA separated by S12 chromatography Activity of *E. coli* expressed α-*N*-acetylgalactosaminidase with the blood group A tetrasaccharide AMC substrate at different pH.

A.

B. % cleavage

Influence of buffer system on enzymatic conversion of $A_2$ cells using *E. coli* expressed α-*N*-acetylgalactosaminidase.

Influence of pH using 250 mM glycine buffer on enzymatic conversion of $A_1$ and $A_2$ cells using *E. coli* expressed α-*N*-acetylgalactosaminidase.

Influence of glycine buffer concentration on enzymatic conversion of $A_1$ cells using *E. coli* expressed α-*N*-acetylgalactosaminidase.

Influence of concentration *E. coli* expressed α-*N*-acetylgalactosaminidase on enzymatic conversion of $A_1$ and $A_2$ cells.

Influence of concentration of cells (hematocrit) on enzymatic conversion of $A_1$ and $A_2$ cells using *E. coli* expressed α-*N*-acetylgalactosaminidase.

Influence of reaction time on enzymatic conversion of $A_1$ and $A_2$ cells using *E. coli* expressed α-*N*-acetylgalactosaminidase.

Influence of temperature on enzymatic conversion of $A_1$ and $A_2$ cells using *E. coli* expressed α-$N$-acetylgalactosaminidase.

```
                         SEQUENCE LISTING

<160> NUMBER OF SEQ ID NOS: 1

<210> SEQ ID NO 1
<211> LENGTH: 8
<212> TYPE: PRT
<213> ORGANISM: Artificial Sequence
<220> FEATURE:
<223> OTHER INFORMATION: Description of Artificial Sequence: Alpha
      galactosidase enzyme

<400> SEQUENCE: 1

Phe Ala Asn Gly Leu Leu Leu Thr
  1               5
```

STREPTOMYCES GRISEOPLANUS COMPRISING AN α-GALACTOSIDASE FOR REMOVING IMMUNODOMINANT α-GALACTOSE MONOSACCHARIDES FROM BLOOD GROUP B OR AB REACTIVE CELLS

RELATED APPLICATIONS

This application is a continuation of U.S. patent application Ser. No. 12/789,946, filed May 28, 2010, now U.S. Pat. No. 7,993,896, which is a divisional application of U.S. application Ser. No. 10/251,271, filed Sep. 20, 2002, now U.S. Pat. No. 7,767,415, which claims benefit of U.S. Provisional Application No. 60/361,769, filed on Mar. 5, 2002, and claims the benefit of U.S. Provisional Application No. 60/324,970, filed on Sep. 25, 2001. The entire teachings of the above applications are incorporated herein by reference.

FIELD OF THE INVENTION

This invention relates to enzymatic removal of type A and B antigens from blood group A, B, and AB reactive cells in blood products, and thereby converting these to non-A and non-B reactive cells. Specifically this invention relates to enzymatic removal of the immunodominant monosaccharides specifying the blood group A and B antigens, namely α1,3-$_D$-galactose and α1,3-$_D$-N-acetylgalactosamine, respectively. More particularly, this invention relates to the use of unique α-N-acetylgalactosaminidases and α-galactosidases with superior kinetic properties for removal of the immunodominant monosaccharides of the blood group A and B antigens and improved performance in enzymatic conversion of red blood cells. Specifically, the preferred unique α-N-acetylgalactosaminidases and α-galactosidases exhibits the following characteristics: (i) exclusive, preferred or no less than 10% substrate specificity for the type A and B branched polysaccharide structures relative to measurable activity with simple mono- and disaccharide structures and aglycon derivatives hereof; (ii) optimal performance at neutral pH with blood group oligosaccharide and in enzymatic conversion of cells; and (iii) a favorable kinetic constant $K_m$ with mono- and oligosaccharide substrates. This invention further relates to methods for use of these unique α-N-acetylgalactosaminidases and α-galactosidases in obtaining complete removal of A and B antigens of type A, B, and AB cells determined by standard blood bank serological typing and cross match analysis. More particularly, this invention relates to methods for conversion of cells using significantly lower amounts of recombinant glycosidase enzyme proteins than previously used and obtaining complete sero-conversion of all blood group A and B red cells.

BACKGROUND OF THE INVENTION

As used herein, the term "blood products" includes whole blood and cellular components derived from blood, including erythrocytes (red blood cells) and platelets.

There are more than thirty blood group or type) systems, one of the most important of which is the ABO system. This system is based on the presence or absence of antigens A and/or B. These antigens are found on the surface of erythrocytes and platelets as well as on the surface of endothelial and most epithelial cells. The major blood product used for transfusion is erythrocytes, which are red blood cells containing hemoglobin, the principal function of which is the transport of oxygen. Blood of group A contains antigen A on its erythrocytes. Similarly, blood of group B contains antigen B on its erythrocytes. Blood of group AB contains both antigens, and blood of group O contains neither antigen.

The blood group structures are glycoproteins or glycolipids and considerable work has been done to identify the specific structures making up the A and B determinants or antigens. The ABH blood group specificity is determined by the nature and linkage of monosaccharides at the ends of the carbohydrate chains. The carbohydrate chains are attached to a peptide (glycoprotein) or lipid (glycosphingolipid) backbone, which are attached to the cell membrane of the cells. The immunodominant monosaccharide determining type A specificity is a terminal α1-3 linked N-acetylgalactosamine (GalNAc), while the corresponding monosaccharide of B type specificity is an α1-3 linked galactose (Gal). Type O cells lack either of these monosaccharides at the termini of oligosaccharide chains, which instead are terminated with α1-2 linked fucose (Fuc) residues.

A great diversity of blood group ABH carbohydrate structures are found due to structural variations in the oligosaccharide chains that carry ABH immunodominant saccharides. Table 1 lists structures reported in man and those that have been found on human red cells or in blood extracts. For a review, see, Clausen & Hakomori, Vox Sang 56(1): 1-20, 1989). Red cells contain ABH antigens on N-linked glycoproteins and glycosphingolipids, while it is generally believed that O-linked glycans on erythrocytes glycoproteins, mainly glycophorins, are terminated by sialic acid and not with ABH antigens. Type 1 chain glycosphingolipids are not endogenous products of red cells, but rather adsorbed from plasma.

TABLE I

Histo-Blood Group ABH Immunoreactive Determinants of Human Cells[1]

| Name | Hapten Structure | Type of Glycoconjugate | Found on RBC | Structure No |
|---|---|---|---|---|
| A type 1, ALe$^d$ | GalNAcα1-3Galβ1-3GlcNAcβ1-R<br>2<br>\|<br>Fucα1 | Glycolipid<br>N-linked<br>O-linked | Glycolipid | 1 |
| A type 1, ALe$^b$ | GalNAcα1-3Galβ1-3 GlcNAcβ1-R<br>2    4<br>\|    \|<br>Fucα1  Fucα1 | Glycolipid<br>N-linked<br>O-linked | Glycolipid | 2 |

TABLE I-continued

Histo-Blood Group ABH Immunoreactive Determinants of Human Cells[1]

| Name | Hapten Structure | Type of Glycoconjugate | Found on RBC | Structure No |
|---|---|---|---|---|
| A type 2, A | GalNAcα1-3Galβ1-4GlcNAcβ1-R<br>　　　　　　2<br>　　　　　　\|<br>　　　　　Fucα1 | Glycolipid<br>N-linked<br>O-linked | Glycolipid<br>N-linked | 3 |
| A type 2, ALe$^y$ | GalNAcα1-3Galβ1-4GlcNAcβ1-R<br>　　　　　　2　　　　　3<br>　　　　　　\|　　　　　\|<br>　　　　　Fucα1　　　Fucα1 | Glycolipid<br>N-linked<br>O-linked | Glycolipid? | 4 |
| A type 3, O-linked | GalNAcα1-3Galβ1-3GalNAcα1-OSer/Thr<br>　　　　　　2<br>　　　　　　\|<br>　　　　　Fucα1 | O-linked | | 5 |
| A type 3, Repetitive | GalNAcα1-3Galβ1-3GalNAcα1-3Galβ1-4GlcNAcβ1-R<br>　　　　　　2　　　　　　　　　2<br>　　　　　　\|　　　　　　　　　\|<br>　　　　　Fucα1　　　　　　　Fucα1 | Glycolipid | Glycolipid | 6 |
| A type 4, Globo | GalNAcα1-3Galβ1-3GalNAcβ1-3Galα1-R<br>　　　　　　2<br>　　　　　　\|<br>　　　　　Fucα1 | Glycolipid | Glycolipid? | 7 |
| A type 4, Ganglio | GalNAcα1-3Galβ1-3GalNAcβ1-3Galβ1-R<br>　　　　　　2<br>　　　　　　\|<br>　　　　　Fucα1 | Glycolipid | | 8 |
| B type 1, BLe$^d$ | Galα1-3Galβ1-3GlcNAcβ1-R<br>　　　　　2<br>　　　　　\|<br>　　　　Fucα1 | Glycolipid<br>N-linked<br>O-linked | Glycolipid | 9 |
| B type 1, BLe$^b$ | Galα1-3Galβ1-3GlcNAcβ1-R<br>　　　　　2　　　　　4<br>　　　　　\|　　　　　\|<br>　　　　Fucα1　　　Fucα1 | Glycolipid<br>N-linked<br>O-linked | Glycolipid | 10 |
| B type 2, B | Galα1-3Galβ1-4GlcNAcβ1-R<br>　　　　　2<br>　　　　　\|<br>　　　　Fucα1 | Glycolipid<br>N-linked<br>O-linked | Glycolipid<br>N-linked | 11 |
| B type 2, BLe$^y$ | Galα1-3Galβ1-4GlcNAcβ1-R<br>　　　　　2　　　　　3<br>　　　　　\|　　　　　\|<br>　　　　Fucα1　　　Fucα1 | Glycolipid<br>N-linked<br>O-linked | Glycolipid? | 12 |
| B type 3, O-linked | Galα1-3Galβ1-3GalNAcα1-O-Ser/Thr<br>　　　　　2<br>　　　　　\|<br>　　　　Fucα1 | O-linked | | 13 |

TABLE I-continued

Histo-Blood Group ABH Immunoreactive Determinants of Human Cells[1]

| Name | Hapten Structure | Type of Glycoconjugate | Found on RBC | Structure No |
|---|---|---|---|---|
| B type 4, Globo | Galα1-3Galβ1-3GalNAcβ1-3Galα1-R<br>　　　　　　　　　　　　2<br>　　　　　　　　　　　Fucα1 | Glycolipid? | Glycolipid? | 14 |
| B type 4, Ganglio | Galα1-3Galβ1-3GalNAcβ1-3Galβ1-R<br>　　　　　　　　　　　　2<br>　　　　　　　　　　　Fucα1 | Glycolipid? | | 15 |
| H type 1, Le$^d$ | Galβ1-3GlcNAcβ1-R<br>　　　　2<br>　　Fucα1 | Glycolipid<br>N-linked<br>O-linked | Glycolipid | 16 |
| H type 1, Le$^b$ | Galβ1-3GlcNAcβ1-R<br>　　2　　　　4<br>Fucα1　　Fucα1 | Glycolipid<br>N-linked<br>O-linked | Glycolipid | 17 |
| H type 2, H | Galβ1-4GlcNAcβ1-R<br>　　　　2<br>　　Fucα1 | Glycolipid<br>N-linked<br>O-linked | Glycolipid<br>N-linked | 18 |
| H type 2, Le$^y$ | Galβ1-4GlcNAcβ1-R<br>　　2　　　　3<br>Fucα1　　Fucα1 | Glycolipid<br>N-linked<br>O-linked | Glycolipid? | 19 |
| H type 3, O-linked | Galβ1-3GalNAcα1-O-Ser/Thr<br>　　　　2<br>　　Fucα1 | O-linked | | 20 |
| H type 3, H-A | Galβ1-3GalNAcα1-3Galβ1-4GlcNAcβ1-R<br>　　2　　　　　　　　2<br>Fucα1　　　　　　　Fucα1 | Glycolipid | Glycolipid<br>(A RBC) | 21 |
| H type 4, Globo | Galβ1-3GalNAcβ1-3Galα1-R<br>　　　　2<br>　　Fucα1 | Glycolipid | Glycolipid | 22 |
| H type 4, Ganglio | Galβ1-3GalNAcβ1-3Galβ1-R<br>　　　　2<br>　　Fucα1 | Glycolipid | | 23 |
| Thomsen-Friedenrich Tf, T | Galβ1-3GalNAcα1-O-Ser/Thr | O-linked | O-linked (+SA) | 24 |

TABLE I-continued

Histo-Blood Group ABH Immunoreactive Determinants of Human Cells[1]

| Name | Hapten Structure | Type of Glycoconjugate | Found on RBC | Structure No |
|---|---|---|---|---|
| Gal-A, T cross-react. | Galβ1-3GalNAcα1-3Galβ1-4GlcNAcβ1-R<br>　　　　　　　2<br>　　　　　　Fucα1 | Glycolipid | Glycolipid (A RBC) | 25 |
| Tn, A cross-react. | GalNAcα1-O-Ser/Thr | O-linked | O-linked (+SA) | 26 |

[1]Adapted from Clausen and Hakomori, Vox Sang 56(1): 1-20, 1989.
Designations: "?" indicates potential gycolipid structures which have not been reported to date.

Blood group A and B exist in several subtypes. Blood group A subtypes are the most frequent, and there are three recognized major sub-types of blood type A. These sub-types are known as $A_1$, A intermediate ($A_{int}$) and $A_2$. There are both quantitative and qualitative differences that distinguish these three sub-types. Quantitatively, $A_1$ erythrocytes have more antigenic A sites, i.e., terminal N-acetylgalactosamine residues, than $A_{int}$ erythrocytes which in turn have more antigenic A sites than $A_2$ erythrocytes. Qualitatively, $A_1$ erythrocytes have a dual repeated A structure on a subset of glycosphingolipids, while $A_2$ cells have an H structure on an internal A structure on a similar subset of glycolipids (Clausen et al., Proc. Natl. Acad. Sci. USA 82(4): 1199-203, 1985, Clausen et al., J. Biol. Chem. 261(3): 1380-7, 1986). These differences between $A_1$ and weak A subtypes are thought to relate to differences in the kinetic properties of blood group A isoenzyme variants responsible for the formation of A antigens (Clausen et al., J. Biol. Chem. 261(3): 1388-92, 1986). The differences of group B subtypes are believed to be solely of quantitative nature.

Blood of group A contains antibodies to antigen B. Conversely, blood of group B contains antibodies to antigen A. Blood of group AB has neither antibody, and blood group O has both. Antibodies to these and other carbohydrate defined blood group antigens are believed to be elicited by continuous exposure to microbial organism carrying related carbohydrate structures. An individual whose blood contains either (or both) of the anti-A or anti-B antibodies cannot receive a transfusion of blood containing the corresponding incompatible antigen(s). If an individual receives a transfusion of blood of an incompatible group, the blood transfusion recipient's antibodies coat the red blood cells of the transfused incompatible group and cause the transfused red blood cells to agglutinate, or stick together. Transfusion reactions and/or hemolysis the destruction of red blood cells) may result therefrom.

In order to avoid red blood cell agglutination, transfusion reactions, and hemolysis, transfusion blood type is cross-matched against the blood type of the transfusion recipient. For example, a blood type A recipient can be safely transfused with type A blood, which contains compatible antigens. Because type O blood contains no A or B antigens, it can be transfused into any recipient with any blood type, i.e., recipients with blood types A, B, AB or O. Thus, type O blood is considered "universal", and may be used for all transfusions. Hence, it is desirable for blood banks to maintain large quantities of type O blood. However, there is a paucity of blood type O donors. Therefore, it is desirable and useful to remove the immunodominant A and B antigens on types A, B and AB blood in order to maintain large quantities of universal blood products.

In an attempt to increase the supply of type O blood, methods have been developed for converting certain type A, B and AB blood to type O blood. Conversion of B cells to type O cells has been accomplished in the past. However, conversion of the more abundant A cells has only been achieved with the less abundant weak A subgroup cells. The major obstacle for development and utilization of enzyme converted universal O cells has, in the past, been the failure to enzymatically convert the strong $A_1$ cells. This obstacle has remained. As will be explained below in detail the enzymes and methods used in the prior art are inefficient, impractical, and/or too costly to be used in a commercial process to supply universal type O cells.

Conversion of B Cells:

Enzymatic conversion of type B blood using purified or recombinant coffee bean (Coffey canephora) α-galactosidase has been achieved using 100-200 U/ml (U.S. Pat. No. 4,427,777; Zhu et al., Arch Biochem Biophys 1996; 327(2): 324-9; Kruskall et al., Transfusion 2000; 40(11): 1290-8). The specific activity of coffee bean α-galactosidase was reported to be 32 U/mg using p-nitrophenyl α-D-Gal with one unit (U) defined as one μmole substrate hydrolyzed per minute (Zhu et al., Arch Biochem Biophys 1996; 327(2): 324-9). Enzymatic conversions were done at pH 5.5 with approximately 6 mg/ml enzyme at 80-90% hematocrit, and the resulting converted O cells functioned normally in transfusion experiments and no significant adverse clinical parameters were observed (Kruskall et al., Transfusion 2000; 40(11): 1290-8). This data along with earlier publications, clearly demonstrate that enzymatic conversion of red blood cells is feasible and that such enzyme group B converted O (B ECO) cells can function as well as matched type untreated cells in transfusion medicine. Nevertheless, the quantities of enzymes used in these studies, even with present days most effective recombinant expression technology, renders ECO cells impractical mainly for economical reasons.

Claims of improved protocols for conversion of B cells using recombinant Glycine max α-galactosidase with a specific activity of approximately 200 U/mg have been reported using 5-10 units/ml with 16% hematocrit (U.S. Pat. Nos. 5,606,042; 5,633,130; 5,731,426; 6,184,017). The Glycine max α-galactosidase was thus used at 25-50 μg/ml, which represents a significant reduction in enzyme protein quantities required (50-200 fold) (Davis et al., Biochemistry and Molecular Biology International, 39(3): 471-485, 1996). This reduction is partly due to the higher specific activity of the *Glycine max* α-galactosidase (approximately 6 fold) as well as different methods used for conversion and evaluation. The 200 U/ml enzyme used in the study of Kruskall et al., (*Transfusion*, 40(11): 1290-8, 2000) was worked out for full unit (approximately 220 ml packed cells) conversions at 80-90% hematocrits and thoroughly analyzed by standard blood bank typing as well as by more sensitive cross-match analysis. Furthermore, the efficiency of conversion was evaluated by analysis of survival and induced immunity in patients receiving multiple transfusions of converted cells. The enzymatic conversions were done in test tubes in ml scale at 16% hematocrit, as described in U.S. Pat. No. 5,606,042 (and U.S. Pat. Nos. 5,633,130; 5,731,426; 6,184,017) with *Glycine max* (α-galactosidase, and the conversion efficiency not evaluated by cross-match analysis. Conversion of cells at 16% hematocrit required 10 U/ml, while conversions at 8% required 5 U/ml, indicating that converting at increased hematocrit requires more enzyme although higher cell concentrations were not tested. Thus, part of the reduction in enzyme protein quantities required compared to protocols reported by Kruskall et al., (*Transfusion* 2000; 40(11): 1290-8), is related to the concentration (hematocrit) of cells used in conversion, and this may represent more than 5-10 fold although direct comparison is not possible without experimentation. The U.S. Pat. No. 5,606,042 (and U.S. Pat. Nos. 5,633,130; 5,731,426; 6,184,017) further provides improvements in the conversion buffer using Na citrate and glycine at less acidic pH (preferably pH 5.8) and including additional protein in the form of BSA (bovine serum albumin) for stabilization. Interestingly, the conversion buffer developed for the *Glycine max* α-galactosidase was found not to be applicable to coffee bean α-galactosidase. Although, some improvement in the conversion of B cells may be provided by U.S. Pat. No. 5,606,042 (and U.S. Pat. Nos. 5,633,130; 5,731,426; 6,184,017), it is clear that at least more than 0.5 mg of enzyme is required per ml packed type B red cells using the disclosed protocol. It is likely that considerable more enzyme than this is required to obtain cells fully converted to O cells by the most sensitive typing procedures used in standard blood bank typing protocols. Furthermore, the protocol requires introduction of additional extraneous protein (BSA or human serum albumin) as well as exposing cells to acidic pH.

It is evident from the above that further improvements in conversion of B cells is required in order to make this a practical and commercially applicable technology. Necessary improvements include obtaining more efficient alpha-galactosidase enzymes, which allow conversion to take place preferable at neutral pH and without extraneous protein added.

Conversion of A Cells:

Levy and Animoff (*J. Biol. Chem.* 255: 1737-42, 1980) tested the ability of purified *Clostridium perfringens* α-N-acetylgalactosaminidase to convert A cells, and found reduction in antigen expression but considerable blood group A activity remained. Further studies of this enzyme have lead to purification to apparent homogeneity with a specific activity using the αGalNAc p-nitrophenyl substrate of 43.92 U/mg (Hsieh et al., *IUBMB Life*, 50(2): 91-7, 2000; PCT Application No. WO 99/23210). The purified enzyme had a neutral pH optimum with the αGalNAc p-nitrophenyl substrate, but no studies of the activity of this enzyme with oligosaccharides were presented. Some degradation of the $A_2$ epitope with the purified enzyme in an ELISA assay was reported, but the enzyme have not been evaluated in enzyme conversion of $A_2$ cells with appropriate blood typing.

Goldstein (*Prog Clin Biol Res* 165: 139-57, 1984; *Transfus Med Rev* 3(3): 206-12, 1989) was unsuccessful in converting A cells using chicken liver α-N-acetylgalactosaminidase. U.S. Pat. No. 4,609,627 entitled "Enzymatic Conversion of Certain Sub-Type A and AB Erythrocytes", is directed to a process for converting $A_{int}$ and $A_2$ (including $A_2B$ erythrocytes) to erythrocytes of the H antigen type, as well as to compositions of type B erythrocytes which lack A antigens, which compositions, prior to treatment, contained both A and B antigens on the surface of said erythrocytes. The process for converting $A_{int}$ and $A_2$ erythrocytes to erythrocytes of the H antigen type, which is described in U.S. Pat. No. 4,609,627, includes the steps of equilibrating certain sub-type A or AB erythrocytes, contacting the equilibrated erythrocytes with purified chicken liver α-N-acetylgalactosaminidase enzyme for a period sufficient to convert the A antigen to the H antigen, removing the enzyme from the erythrocytes and re-equilibrating the erythrocytes. U.S. Pat. No. 6,228,631 entitled "Recombinant α-N-acetylgalactosaminidase enzyme and cDNA encoding said enzyme" provides a recombinant source for the chicken enzyme. The specific activities of purified and recombinant *Pichia pastoris* produced chicken liver α-N-acetylgalactosaminidase were reported to be approximately 51-56 U/mg using p-nitrophenyl αGalNAc as substrate (Zhu et al., Protein Expression and Purification 8: 456-62, 1996). The described conversion conditions for $A_{int}$ and $A_2$ cells in U.S. Pat. No. 4,609,627 included 180 U/ml cells (hematocrit not specified) at acidic pH 5.7, and treated cells did not agglutinate with unspecified anti-A reagent. This protocol requires more than 3 mg/ml enzyme protein and has not been reported to convert type $A_1$ cells.

Hata et al. (*Biochem Int.* 28(1): 77-86, 1992) also reported conversion of $A_2$ cells using chicken liver α-N-acetylgalactosaminidase at acidic pH. U.S. Pat. No. 5,606,042 (and U.S. Pat. Nos. 5,633,130; 5,731,426; 6,184,017) disclose similar results.

Falk et al. (*Arch Biochem Biophys* 290(2): 312-91991, 1991) demonstrated that an α-N-acetylgalactosaminidase purified from *Ruminococcus torques* strain IX-70 could destroy *Dolichus biflorus* agglutinability indicating that the A antigenic strength of $A_1$ cells was reduced to the level of $A_2$ cells.

Izumi et al. (*Biochem Biophys Acta* 1116: 72-74, 1992) tested purified *Acremonium* sp. α-N-acetylgalactosaminidase on type $A_1$ cells. Although some reduction in agglutination titer was observed using 7,000 U/ml (140 U/20 µl) 4% hematocrit, conversion was not complete.

Human α-N-acetylgalactosaminidase enzyme has been isolated, cloned and expressed (Tsuji et al., Biochem. Biophys. Res. Commun. 163: 1498-1504, 1989, Wang et al., Human α-N-acetylgalactosaminidase-molecular cloning, nucleotide sequence, and expression of a full-length cDNA. Homology with human alpha-galactosidase A suggests evolution from a common ancestral gene. J Biol. Chem. 265: 21859-66, 1990) (U.S. Pat. No. 5,491,075). The pH optimum of human α-N-acetylgalactosaminidase is 3.5 (Dean K J, Sweeley C C. Studies on human liver alpha-galactosidases. II. Purification and enzymatic properties of alpha-galactosidase B (alpha-N-acetylgalactosaminidase). J Biol. Chem. 254: 10001-5, 1979), similar to that of the human α-galactosidase (Dean K J, Sweeley C C. Studies on human liver alpha-galactosidases. I. Purification of alpha-galactosidase A and its enzymatic properties with glycolipid and oligosaccharide substrates. J Biol. Chem. 254: 9994-10000, 1979).

It is evident from the above that enzymatic conversion of type A cells, and particularly subgroup $A_1$ cells constituting up to 80% of group A, has not been accomplished to date. Therefore, there exists a need in the prior art to identify appropriate enzymes capable of converting group A cells by removing all immunoreactive A antigens. Furthermore, there exists a need to develop appropriate conversion conditions preferably at neutral pH and without requirement of additional extraneous proteins.

Screening Assays:

Previous methods for searching, identification and characterization of exo-glycosidases have generally relied on the use of simple monosaccharide derivatives as substrates to identify saccharide and potential linkage specificity. Derivatized monosaccharide, or rarely oligosaccharide, substrates include without limitations p-nitrophenyl (pNP), benzyl (Bz), 4-methyl-umbrelliferyl (Umb), and 7-amino-4-methyl-coumarin (AMC). The use of such substrates provides easy, fast, and inexpensive tools to identify glycosidase activities, and makes large scale screening of diverse sources of enzymes practically applicable. However, the kinetic properties and fine substrate specificities of glycosidase enzymes may not necessarily be reflected in assays with such simple structures. It is also possible that novel enzymes with high degree of specificity and/or selective efficiency for complex oligosaccharide and unique glycoconjugate structures exists, but that these may have been overlooked and remain unrecognized due to methods of analysis. Thus, in order to identify and select the optimal exo-glycosidase for a particular complex oligosaccharide or glycoconjugate structure it may be preferable to use such complex structures in assays used for screening-sources of enzymes. Furthermore, assays used for screening may include selection for preferable kinetic properties such as pH requirement and performance on substrates, e.g., attached to the membrane of cells.

In the prior art, all α-galactosidases (EC 3.2.1.22) and α-N-acetylgalactosaminidases (EC 3.2.1.49) used for destroying B and A antigens of blood cells have been identified and characterized using primarily p-nitrophenyl monosaccharide derivatives. Interestingly, all α-galactosidase and α-N-acetylgalactosaminidase enzymes used in past studies to attempt removal of A and B antigens on cells are evolutionary homologous as evidenced by significant DNA and amino acid sequence similarities. Thus, the human α-galactosidase and α-N-acetylgalactosaminidase are close homologues (Wang et al., *J Biol Chem*, 265: 21859-66, 1990), and other enzymes previously used in blood cell conversion including the chicken liver α-N-acetylgalactosaminidase, fungal *acremonium* α-N-acetylgalactosaminidase, and bacterial α-galactosidases all exhibit significant sequence similarities. Primary structures of bacterial α-N-acetylgalactosaminidases have not been reported in the scientific literature. Because these glycosidases share sequence similarity it may be anticipated that the enzymes have related kinetic properties. Sequence analysis of all known O-glycoside hydrolases have been grouped in 85 distinct families based on sequence analysis, and the above mentioned α-galactosidases and α-N-acetylgalactosaminidases are grouped in families 27 and 36 (see, e.g., the webpage entitled "CAZy—Carbohydrate-Active Enzymes (Family GH32)" and located at afmb.cnrs-mrs.fr/.aboutcazy./CAZY/GH 32.html-. These enzymes are characterized by having a retaining mechanism of catalysis and use aspartic acid as the catalytic nucleophile (Henrissat, *Biochem Soc Trans*, 26(2): 153-6, 1998; Rye & Withers, *Curr Opin Chem Biol*, 4(5): 573-80, 2000).

Therefore, there exists in the art a need to identify new α-galactosidase and α-N-acetylgalactosaminidase activities and corresponding enzyme proteins. If such enzymes exist, it is likely that they would not classify within families 27 and 36 because they would be selected to have significantly different kinetic properties.

SUMMARY OF THE INVENTION

The present invention provides compositions and methods for the enzymatic removal of type A and B antigens from blood group A, B, and AB reactive cells in blood products, and the conversion of these to non-A and non-B reactive cells. Specifically, this invention provides compositions and methods for enzymatic removal of the immunodominant monosaccharides specifying the blood group A and B antigens, namely α1,3-$_D$-galactose and α1,3-$_D$-N-acetylgalactosamine, respectively.

The novel glycosidase enzymes of the present invention have been specifically selected for use in the removal of the immunodominant monosaccharides, αGalNAc and αGal, from complex oligosaccharide targets close to the true A and B carbohydrate antigens of the surface of cells in blood products. Preferred α-N-acetylgalactosaminidase enzymes of this invention have the following characteristics: (i) no less than 10% activity with blood group A oligosaccharides (tetrasaccharide or higher) compared to simple α-GalNAc monosaccharide derivatives; and (ii) active in red blood cell conversion at neutral pH (pH 6-8) with blood group A oligosaccharides. The α-N-acetylgalactosaminidases of the present invention remove all detectable A antigens of all group A cells, including group $A_1$. Preferred α-galactosidase enzymes of this invention have the following characteristics: (i) no less than 10% activity with blood group B oligosaccharides (tetrasaccharide or higher) compared to simple α-Gal monosaccharide derivatives; and (ii) active in red blood cell conversion at neutral pH (pH 6-8) with blood group B oligosaccharides. The α-galactosidase enzymes of the present invention have no detectable activity with $P_1$ antigens. More preferred acetylgalactosaminidase and α-galactosidase enzymes are of bacterial or fungal origin, thereby permitting efficient and inexpensive recombinant expression in prokaryotic and lower eukaryotic cells. In a preferred embodiment, the enzymes of this invention have no detectable activity with p-nitrophenyl monosaccharide derivatives. In another preferred embodiment, enzymes of this invention have a favorable kinetic constant $K_m$ with mono- and oligosaccharide substrates. A particularly preferred α-galactosidase enzyme is further characterized as migrating in the 40-80 kD region by reducing SDS-PAGE analysis. Another particularly preferred α-galactosidase enzyme comprises the amino acid sequence:

(SEQ ID NO: 1)
Phe-Ala-Asn-Gly-Leu-Leu-Leu-Thr.

In another aspect, this invention provides methods for the complete sero-conversion of all blood group A and B red cells, resulting in the complete removal of A and B antigens from type A, B, and AB cells. The removal of A and/or B antigens can be determined by standard blood bank serological typing or cross match analysis. According to the methods of this invention, the A and B antigens are removed using the α-N-acetylgalactosaminidases and/or α-galactosidases that (i) have no less than 10% activity with blood group A or B oligosaccharides (tetrasaccharide or higher) compared to simple mono- and disaccharide structures and aglycon derivatives; and (ii) are active in red blood cell conversion at neutral pH (pH 6-8). In a preferred embodiment, these sero-conversion methods using significantly lower amounts of recombinant glycosidase enzyme proteins than methods known in the art. These methods comprise the steps of: (a) contacting the blood product with the enzyme, under neutral pH conditions, for a period sufficient to remove the antigens, and (b) removing the enzyme from the blood product.

In one embodiment, this invention provides methods for the removal of all detectable A antigens from group A or AB red cells, including group $A_1$, using α-N-acetylgalactosaminidases that (i) have no less than 10% activity with blood group A oligosaccharides (tetrasaccharide or higher) compared to simple α-GalNAc monosaccharide derivatives; and (ii) are active in red blood cell conversion at neutral pH (pH 6-8) with blood group A oligosaccharides.

In another embodiment, this invention provides methods for the removal of all detectable B antigens from group B or AB red cells, using α-galactosidases that (i) have no less than 10% activity with blood group B oligosaccharides (tetrasaccharide or higher) compared to simple α-Gal monosaccharide derivatives; and (ii) are active in red blood cell conversion at neutral pH (pH 6-8) with blood group oligosaccharides.

In yet another embodiment, this invention provides methods for the removal of all detectable A and B antigens from group AB red cells using an α-N-acetylgalactosaminidases and an α-galactosidases, each having one or more of the following characteristics: (i) have no less than 10% activity with oligosaccharide structures (tetrasaccharide or higher) compared to simple mono- and disaccharide structures and aglycon derivatives; and (ii) are active in red blood cell conversion at neutral pH (pH 6-8) with blood group oligosaccharides.

In another aspect of the present invention, there are provided sero-converted erythrocytes. In one embodiment, the sero-converted erythrocytes are characterized as: (i) having been converted from a type A or type AB erythrocyte to a non-A erythrocyte by an α-N-acetylgalactosaminidase; (ii) having A associated H structures; and (iii) having no detectable A antigens, including $A_1$ antigens, as determined by standard blood bank serological typing and cross match analysis. In another embodiment, the sero-converted erythrocytes are characterized as: (i) having been converted from a type B or type AB erythrocyte to a non-B erythrocyte by an α-galactosidase; (ii) having retained $P_1$ antigenicity if of $P_1$ blood group; and (iii) having no detectable B antigens, as determined by standard blood bank serological typing or cross match analysis. In yet another embodiment, the sero-converted erythrocytes are characterized as: (i) having been converted from a type AB erythrocyte to a non-A, non-B erythrocyte by an α-N-acetylgalactosaminidase and an α-galactosidase; (ii) having A associated H structures; and (iii) having retained $P_1$ antigenicity if of $P_1$ blood group; and (iii) having no detectable B antigens, as determined by standard blood bank serological typing or cross match analysis.

In yet another aspect, this invention provides methods for the screening and selection of enzymes with the above described preferred unique characteristics and methods of purification and amino acid sequencing useful for cloning and expression of the genes encoding these enzymes. These methods provide bacterial isolates producing such preferred enzymes.

In one embodiment, the method for screening and selecting an α-galactosidase enzyme useful for removing type B antigens from blood group B and AB reactive cells in blood products under neutral pH conditions comprises the step of: (a) contacting a candidate α-galactosidase enzyme, under neutral pH conditions, with a group B oligosaccharide substrate and measuring the activity of the candidate enzyme with the group B oligosaccharide substrate; (b) contacting said candidate α-galactosidase enzyme, under neutral pH conditions, with an α-Gal monosaccharide derivative and measuring the activity of the candidate enzyme with the group B monosaccharide derivative; and (c) comparing the relative activity of the candidate enzyme with the group B oligosaccharide substrate and α-Gal monosaccharide derivative. Candidates having no less than 10% activity with blood group B oligosaccharides (tetrasaccharide or higher) compared to simple α-Gal monosaccharide derivatives are selected as useful for removing type B antigens from blood group B and AB reactive cells in blood products under neutral pH conditions.

In another embodiment, the method for screening and selecting an α-N-acetylgalactosaminidase enzyme useful for removing type A antigens from blood group A and AB reactive cells in blood products under neutral pH conditions comprises the step of: (a) contacting a candidate α-N-acetylgalactosaminidase enzyme, under neutral pH conditions, with a group A oligosaccharide substrate and measuring the activity of the candidate enzyme with the group A oligosaccharide substrate; (b) contacting said candidate α-N-acetylgalactosaminidase enzyme, under neutral pH conditions, with an α-GalNAc monosaccharide derivative and measuring the activity of the candidate enzyme with the group A monosaccharide derivative; and (c) comparing the relative activity of the candidate enzyme with the group A oligosaccharide substrate and α-GalNAc monosaccharide derivative. Candidates having no less than 10% activity with blood group A oligosaccharides (tetrasaccharide or higher) compared to simple α-GalNAc monosaccharide derivatives are selected as useful for removing type A antigens from blood group A and AB reactive cells in blood products under neutral pH conditions.

Figure 17:
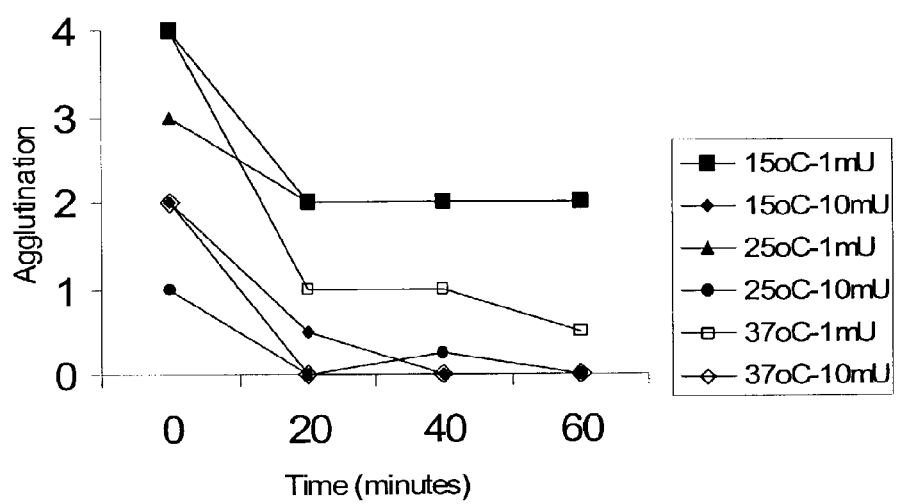

FIG. 17 illustrates the influence of temperature on enzymatic conversion of $A_2$ cells using E. coli expressed α-N-acetylgalactosaminidase. Washed red cells were incubated with 1-10 mU/ml α-N-acetylgalactosaminidase in 200 mM Glycine pH 5.5 at 15° C., 25° C., and 37° C. (30% cell suspension), and conversion evaluated at 20, 40, and 60 min by agglutination with Ortho anti-A.

DETAILED DESCRIPTION OF THE INVENTION

This invention is directed to the development and application of a screening and selection strategy for novel α-N-acetylgalactosaminidases and α-galactosidases with preferred specificities for the blood group A and B structures and with preferred performance in enzymatic conversion of blood cells at neutral pH. Table 1 lists the complex structures of A and B antigens found on blood cells. Quantitative studies of the kinetic properties of existing glycosidases with these complex structures have not been reported. This is due partly to the difficulties in obtaining these compounds from natural sources and partly because of the difficulty and time-consuming efforts involved in synthesizing such complex oligosaccharides by organic chemistry.

For the purpose of this invention, blood group A and B active oligosaccharide AMC derivatives were synthesized (structures 3, 6, 11, 25), and H variants hereof were either synthesized or produced by enzymatic removal of αGal or αGalNAc from the former structures. Furthermore, glycosphingolipids with structures 3, 6, 21, and 25 were purified from human erythrocytes or produced therefrom by glycosidase treatments as previously described (Clausen et al., Proc. Natl. Acad. Sci. USA 82(4): 1199-203, 1985, Clausen et al., J Biol. Chem. 261(3): 1380-7, 1986, Clausen et al., Biochemistry 25(22): 7075-85, 1986, Clausen et al., J Biol. Chem. 262(29): 14228-34, 1987). Thin-layer chromatography assays to quantitatively determine removal of αGal or αGalNAc from the AMC derivatives or glycosphingolipids were developed.

Our initial analysis of the relative specific activities of recombinant coffee bean α-galactosidase comparing activities with p-nitrophenyl α-galactoside and a tetrasaccharide group B hapten substrate (structure 11 AMC derivative) as representative of blood group B antigens revealed a striking difference of nearly 2000 fold. Thus, the coffee bean α-galactosidase had a specific activity of approximately 30-40 U/mg at pH 6.5 with p-nitrophenyl α-galactoside, as previously reported (Zhu et al., Arch Biochem Biophys 324: 65-70, 1995), but only 17 mU/mg with the tetrasaccharide group B substrate. This enzyme is therefore relatively inefficient in destroying group B antigens, and an enzyme with preference for the B tetrasaccharide is likely to exhibit much better kinetic efficiency with group B structures.

Our initial analysis of the relative specific activities of recombinant chicken liver α-N-acetylgalactosaminidase comparing activities with p-nitrophenyl α-N-acetylgalactosamine and a tetrasaccharide group A hapten substrate (structure 3 AMC derivative) as representative of blood group A antigens again revealed a striking difference of over 100 fold. Thus, the chicken α-N-acetylgalactosaminidase as reported previously had a specific activity of approximately 50 U/mg at pH 3.65 with p-nitrophenyl α-N-acetylgalactosamine (Zhu et al., Protein Exp and Purification 8: 456-462, 1996), but only 0.2 U/mg at pH 5.5 (0.3 U/mg at pH 3.65) with the tetrasaccharide group A substrate. This enzyme is therefore relatively very inefficient in destroying group A antigens.

Since these two enzymes constitute state of the art performance in enzymatic conversion of blood cells, and that these either have failed to convert cells (group A) or are impractical due to enzyme quantities required (group B), in addition to both enzymes only performing in blood cell conversion at acidic pH, it is clear that improved kinetic properties of enzymes for use in blood conversion are needed, and that one likely strategy for initial identification is to analyze ratio of activities with p-nitrophenyl and complex A/B substrates. Enzymes with preferred or exclusive activities for the group A or B complex substrates are likely to perform more efficient in blood cell conversion.

Past difficulties in converting group A blood cells have mainly been due to inability to convert the strong $A_1$ subgroup. As described above the group $A_1$ subgroup have more A antigens than other subgroups, but also contain a repeated A structure in the form of glycosphingolipids (Table 1, structure 6). $A_2$ and possible weaker subgroups also contain an A extended series of glycosphingolipids designated H-A and Gal-A (Table 1, structures 21 and 25), but these do not react with anti-A antibodies as originally described by Clausen et al., (Clausen et al., Proc. Natl. Acad. Sci. USA 82(4): 1199-203, 1985, Clausen et al., J Biol. Chem. 261(3): 1380-7, 1986, Clausen et al., Biochemistry 25(22): 7075-85, 1986, Clausen et al., J Biol. Chem. 262(29): 14228-34, 1987). This is further confirmed by the findings that extensive α-N-acetylgalactosaminidase treated subgroup $A_2$ cells type as O with typing reagents as described above. The difficulty in converting subgroup $A_1$ in comparison to subgroup $A_2$ may therefore be due to the quantitative difference in amounts of A antigens, the presence of repetitive A glycosphingolipids on $A_1$ cells only, or a combination of these. An important parameter of preferred α-N-acetylgalactosaminidases for use in group A conversion is the ability to efficiently cleave the terminal αGalNAc residue on repetitive A glycosphingolipids. Analysis of the efficiency of the recombinant chicken liver α-N-acetylgalactosaminidase revealed comparable specific activities (approximately 0.3 U/mg) with A type 2 tetrasaccharide AMC derivative (structure 3) and repetitive A type 3 AMC derivative (structure 6). It may be concluded from this that the failure of the chicken liver α-N-acetylgalactosaminidase to convert all group A cells is not due to the unique $A_1$ structures. Furthermore, this data may indicate that A tetrasaccharides contain sufficient structure of the group A (and B) antigens to be used to determine the kinetic properties and specificities of α-N-acetylgalactosaminidases, as well as for prediction of their performance in blood cell conversion.

Preferred α-N-acetylgalactosaminidases and α-galactosidases have neutral pH optima and can be produced cost-effectively as recombinant proteins in unicellular organisms such as bacteria and yeast. The present invention developed a screening assay for the preferred enzyme activities using A and B tetrasaccharide AMC derivative substrates and measuring activities at neutral pH. Further, activities were compared to activities using p-nitrophenyl monosaccharide derivatives in order to identify activities with preference or exclusivity for the complex substrates. Application of this screening assay on a large panel of bacterial and fungal isolates (3100) identified several bacterial isolates expressing α-N-acetylgalactosaminidase or α-galactosidase activities measured with A or B tetrasaccharide AMC substrates, but no or insignificant levels of activity with the corresponding p-nitrophenyl monosaccharide substrates. One of each activities were further analyzed after sero- and genotyping these as Streptomyces strains. Analysis of strain #8 determined to express α-N- acetylgalactosaminidase activity revealed that the activity was insoluble and associated with the cell mass. Strain #8 was deposited on Feb. 14, 2002 with the American Type Culture Collection (ATCC) and has been assigned ATCC Deposit No. PTA-4076. In contrast, strain #2357 determined to express α-galactosidase activity revealed that the activity was soluble and found in the supernatant of a French press. Strain #2357 was deposited on Feb. 14, 2002 with the American Type Culture Collection and has been assigned ATCC Deposit No. PTA-4077. Because it is considerable simpler to purify a soluble protein, we chose to initially purify and sequence the enzyme protein from #2357. The activity of #2357 was purified to a specific activity of more than 10 U/mg with the B tetrasaccharide substrate, while no activity with p-nitrophenyl α-galactoside was detectable. SDS-PAGE analysis of the resulting preparation revealed 3-4 protein bands in the 40-80 kD region. Gel filtration analysis of the preparation showed activity migrating comparable to BSA indicating a molecular weight of 40-80 kD. A single short sequence was obtained:

SEQ ID NO: 1
Phe-Ala-Asn-Gly-Leu-Leu-Leu-Thr.

Detailed analysis of the substrate specificity of the partially purified α-galactosidase activity demonstrated an unprecedented fine specificity for the branched B blood group structure, and no linear structures capped by α1-3 or α1-4 galactose residues were cleaved. Analysis of pH optimum showed this to be 5.5 to 7.0. The identified α-galactosidase activity is therefore highly preferred over enzymes in the prior art with respect to restricted substrate specificity, high specific activity for group B structures, and pH optimum.

Preliminary analysis of the α-N-acetylgalactosaminidase activity of #8 revealed similar properties, but linear structures were cleaved as well. Due to difficulties in purification it was not possible to assess the specific activity of this enzyme, but even partially purified preparations at 0.1 U/mg, showed no detectable activity with the p-nitrophenyl monosaccharide derivative.

The finding that the two identified and partially characterized activities were similar in nature, and entirely different from any previously reported α-galactosidase and α-N-acetylgalactosaminidase activities, strongly suggested that a unique novel family of homologues glycosidases was identified by the screening strategy employed.

We next embarked on assaying all commercially available α-galactosidases and α-N-acetylgalactosaminidases using our selecting assay to determine if enzymes with the preferred specificity were available. One α-N-acetylgalactosaminidase (NEB α-N-acetylgalactosaminidase) was identified that exhibited relative high substrate specificity for A tetra- and heptasaccharide AMC derivatives compared to the simple αGalNAc monosaccharide derivatives. This enzyme is disclosed by the supplier (New England BioLabs Inc, catalog no. P0734B) to be derived from a proprietary strain and expressed in *E. coli*, and its substrate specificity described as catalyzing the hydrolysis of terminal α-GalNAc linkages from oligosaccharides. Specifically, it is disclosed in material supplied with the enzyme that the substrate specificity include p-nitrophenyl-α-$_D$-N-acetylgalactosaminopyranoside (p-nitrophenyl α-GalNAc) and A tetrasaccharide AMC substrate (structures 3-8). We have not found additional information in the scientific literature or elsewhere as regards this enzyme. Analysis of the kinetic properties of this enzyme with our panel of substrates revealed that the enzyme has a specific activity of approximately 0.25 U/mg with the A tetrasaccharide AMC substrate, and less than 2.5 U/mg with p-nitrophenyl αGalNAc. Furthermore, the enzyme has a broad pH optimum 6.0-8.0. Although, this enzyme only exhibits a moderate preferential substrate specificity for the A tetrasaccharide AMC substrate and the specific activity with this substrate is relatively low, this enzyme partly has the proposed properties of an optimal enzyme to be used in blood cell conversions and it can be expressed in bacteria.

As described above the identified *Streptomyces* α-galactosidase has a specific activity with the B tetrasaccharide substrate exceeding 10 U/mg and it functions at maximum velocity at neutral pH. The enzyme was, however, not available in quantities and of purity required for evaluation of its performance in blood cell conversion. The identified *Streptomyces* α-N-acetylgalactosaminidase was similarly not available. Since the NEB α-N-acetylgalactosaminidase has the same identifying characteristics as the two identified *Streptomyces* activities, although the specific activity is only approximately 0.25 U/mg with the A tetrasaccharide substrate, the availability of this in recombinant pure form allowed for evaluation of this new class of glycosidases in blood cell conversions.

We therefore tested the performance of the NEB α-N-acetylgalactosaminidase in group A blood cell conversion, in order to confirm that the proposed preferred properties of α-N-acetylgalactosaminidases used in the above screening and selection strategy actually selected for enzymes with improved characteristics in enzymatic conversion of red blood cells. The NEB α-N-acetylgalactosaminidase showed remarkable efficiency in conversion of both $A_1$ and $A_2$ blood cells at neutral pH. Using a fixed hematocrit of 30% in enzyme reactions, a number of parameters of the conversion process were analyzed. The preferable buffer system is 200-300 mM glycine at pH 6.5 to 7.5. Several additives may be added to this including but without limiting 1-5 mM NaCl, 1-5 mM $CaCl_2$, 1-10 mM phosphate buffered citrate, 0.25 mM Trisodium citrate, and 0.1 to 10% polyethylene glycol (PEG) of varying molecular weights from 300 to 10,000. Approximately 5 mU/ml NEB α-N-acetylgalactosaminidase converted $A_2$ cells and approximately 20 mU/ml converted $A_1$ cells in 60 minutes (30% hematocrit) to cells typing as O with routine blood banking reagents and procedures. Increased amount of enzyme used resulted in decreased time required for conversion. Converted cells reacted with anti-H reagents as O cells, and analysis of physical parameters of converted cells revealed no changes from untreated cells (methemoglobin, 2,3DPG, ATP and Osmotic fragility). To the best of our knowledge, this is the first example of enzymatic conversion of intact group $A_1$ cells to cells typing as O.

The quantity of *E. coli* expressed α-N-acetylgalactosaminidase required for conversion of group A cells (5-20 mU/ml) is equivalent to 20-80 ug/ml enzyme protein. This is a considerable improvement over amounts of α-acetylgalactosaminidase used in the prior art to convert $A_2$ cells (3 mg/ml). It is also an improvement compared to the quantities of α-galactosidase used to convert B cells, whether it is the coffee bean α-galactosidase (6 mg/ml at 80% hematocrit) or the *Glycine max* α-galactosidase (50 μg/ml at 16% hematocrit). Furthermore, the conversions with NEB α-N-acetylgalactosaminidase were performed at neutral pH, while all other conversions in the past have been done at acidic pH 4.5-5.8.

The performance of the *E. coli* expressed α-N-acetylgalactosaminidase therefore clearly confirms that the properties of this proposed new class of exo-glycosidases, as defined by the criteria set out above, have improved performance in A and B blood cell conversions. Furthermore, the identification and characterization of a *Streptomyces* α-galactosidase with over 40 fold higher specific activity for the blood group B tetrasaccharide substrate compared to the specific activity of the NEB α-N-acetylgalactosaminidase for group A the tetrasaccharide, indicates that the *Streptomyces* enzyme may require more than 40 fold less protein in conversions, i.e., 0.5-2 μg/ml at 30% hematocrit in reactions. Conversion of a unit of packed blood cells (approximately 220 ml) would thus require less than 0.35-1.4 mg/unit. With present bacterial, yeast and fungal expression technologies, it is possible to produce recombinant enzymes at 5-10 US$/mg. It is therefore evident that enzymatic conversion of blood cells requires enzymes with the characteristics and performance of the ones provided by this invention.

Strains 8 and 2357 were both deposited on Feb. 14, 2002 with the American Type Culture Collection and have been assigned ATCC Deposit Nos. PTA-4076 and PTA-4077, respectively. These deposits with the ATCC were made under the teens of the Budapest Treaty on the International Recognition of the Deposit of Microorganisms for the Purpose of Patent Procedure. Applicants acknowledge their duty to replace the deposit should the depository be unable to furnish a sample when requested due to the condition of the deposit before the end of the term of a patent issued hereon. Applicants also acknowledge their responsibility to notify the ATCC of the issuance of such a patent, at which time the deposit will be made available to the public. Prior to that time, the deposit will be made available to the Commissioner of Patents under the terms of 37 C.F.R. §1.14 and 35 U.S.C. §112.

EXAMPLES

General Methods Used:

A series of complex blood group ABH oligosaccharide structures as 7-amino-4-methyl-coumarin derivatives were custom synthesized by Alberta Chemical Research Council as listed in Tables II, III, and IV. Other structures were available from different suppliers (Sigma, CalbioChem, New England Biolabs). Enzymes were prepared as previously reported (Zhu et al., *Protein Expr Purif* 8(4): 456-62, 1996, Zhu et al., *Arch Biochem Biophys.* 324(1): 65-70, 1995), or purchased from suppliers as indicated. All reagents used were of analytical grade or higher. Standard enzyme assays were performed as following with the different glycosidases:

Recombinant Coffee Bean α-galactosidase Expressed in *P. pastoris:*

Assays with p-nitrophenyl monosaccharide derivatives were performed by two procedures:
i) 1.25 μmol substrate in reaction mixtures of a total volume of 0.5 ml containing 50 mM sodium citrate and 20 mM sodium phosphate (pH 5.5) was incubated at 26° C. for 10 min. Reactions were quenched by adding an equal volume 0.2 M sodium borate buffer (pH 9.8). The amount of the liberated p-nitrophenol was determined by measuring the absorbance at 405 nm compared to a standard curve of p-nitrophenol (0.01-0.15 μmole);
ii) 1.25 μmol substrate in reaction mixtures of a total volume of 0.5 ml containing 50 mM sodium citrate and 20 mM sodium phosphate (pH 5.5) was incubated at 26° C. Five μA aliquots were taken at different time points (0', 5', 15', 30', 60') to follow product development. Product development was analyzed by high performance thin-layer chromatography (HPTLC) in chloroform-methanol-water (vol/vol/vol: 60/35/8) visualized by orcinol staining.

Assays with Derivatized oligosaccharide substrates (AMC, OGr) were performed by the following procedure:
iii) One (AMC) or 5 (OGr) nmol substrate in reaction mixtures of a total volume of 10 μl containing 50 mM sodium citrate (pH 6.0) was incubated at 26° C. Aliquots of 2.5-3.0 μl were taken at different time points (0', 15', 30', 60') to follow product development. Product development was analyzed by HPTLC in chloroform-methanol-water (vol/vol/vol: 60/35/8) and visualized by UV or orcinol staining.

Assays with free oligosaccharide substrates were performed by the following procedure:
iv) 5 nmol substrate was incubated in a 10 μl reaction volume containing 50 mM sodium citrate (pH 6.0) at 26° C. or 30° C. for 30-180 min. Product development was analyzed by HPTLC in chloroform-methanol-water (vol/vol/vol: 30/60/10) and visualized by orcinol staining.

Assays to determine $K_m$ for substrates were modified as follows:
v) The concentration of the αGal p-nitrophenyl substrate was varied from 5.0 mM to 0.04 mM (5 μmol/10 μl) using 0.1-0.5 μg enzyme.

Recombinant Chicken Liver α-N-acetylgalactosaminidase Expressed in *P. pastoris:*

Assays with p-nitrophenyl monosaccharide derivatives were performed by two procedures:
vi) 1.25 μmoles of αGalNAc p-nitrophenyl monosaccharide was incubated in a tube containing 50 mM sodium citrate 20 mM sodium phosphate at pH 2.8 at 37° C. for 60 min. 5.0 μl aliquots were taken at different time points (0', 15, 30', 60') to follow the kinetics of product development. Product development was analyzed by high performance thin-layer chromatography (HPTLC) in chloroform-methanol-water (vol/vol/vol: 60/35/8) stained with p-anisaldehyde and visualized by UV.

Commercial Recombinant α-N-acetylgalactosaminidase (New England Biolabs):
vii) 0.5 mM as a starting concentration of αGalNAc p-nitrophenyl monosaccharide derivative in a tube containing 0.05 M Sodium phosphate buffer pH 7.0 was sequentially diluted 2 fold by mixing it with an equal volume of buffer. 0.5 μg of enzyme was added to each tube and incubated for 10 min at 37° C. The reaction was quenched by adding an equal volume of 0.2 M sodium borate buffer (pH 9.8). The amount of the liberated p-nitrophenol was determined by measuring the absorbance at 405 rim.

Example 1

Characterization of Fine Substrate Specificities of α-N-Acetylgalactosaminidases and α-Galactosidases Previously Used in A/B Blood Cell Conversions To eliminate the B and A antigenic activities of red cells, the most efficient exoglycosidases used in the past have been the coffee bean α-galactosidase and the chicken liver α-N-acetylgalactosaminidase, respectively. These enzymes have been studied extensively and their characteristics and performance in red cell conversion described in the literature and in patent applications as referenced above.

(i) Specific Activity with Different Substrates (U/mg).

Table II lists reported specific activities of these enzymes with p-nitrophenyl monosaccharide derivatives. One unit is defined as the activity converting one micromole of substrate in one minute under the optimate assay conditions defined.

Assays with p-nitrophenyl substrates were evaluated at initial velocity with less than 10% of the substrates used.

TABLE II

Specific activities of α-galactosidases and
α-N-acetylgalactosaminidases with monosaccharide derivatives

| Substrate Structure (derivative) | Blood Group Specificity | Recombinant Coffee Bean α-galactosidase pH 6.5 | Recombinant Chicken Liver α-N-acetyl-galactos-aminidase pH 3.65 | Glycine Max. α-galactos-idase pH 6.5 |
|---|---|---|---|---|
| Galα1-pNP | — | 32 U/mg[1] | — | 295.6 U/mg[2] |
| GalNAcα1-pNP | — | — | 50 U/mg[3] | — |

[1]Zhu et al., (1995) *Arch Biochem Biophys* 324: 65-70,
[2]Davis et al., (1996) *Biochem Mol Biol Int* 39: 471-85,
[3]Zhu et al., (1996) *Protein Exp and Purification* 8: 456-462.

In the present invention, similar results were obtained for recombinant purified coffee bean α-galactosidase and the chicken liver α-N-acetylgalactosaminidase. Information of the specific activities with oligosaccharide substrates resembling the A and B antigens have not been reported. This is likely due to limited availability of such compounds. In the present invention, complex A and B structures were synthesized and analysis of the kinetic parameters of the enzymes with substrates mimicking the antigens as found on red cells was predicted to aid in defining criteria for selecting novel enzymes with better properties in red cell conversion.

As shown in Table III, analysis of the specific activities of the two enzymes with the tetrasaccharide AMC derivatives were dramatically lower than the activities obtained with p-nitrophenyl monosaccharide derivatives.

TABLE III

Specific activities of α-galactosidases and
α-N-acetylgalactosaminidases with blood group
active oligosaccharide derivatives[1].

| Substrate Structure (derivative) | Blood Group Specificity | Recombinant Coffee Bean α-galactosidase pH 5.5 | Recombinant Chicken Liver α-N-acetylgalactos-aminidase pH 3.65 | pH 5.5 |
|---|---|---|---|---|
| Galα1-3(Fucα1-2)Galβ1-4GlcNAc-AMC | B | 0.017 U/mg | — | — |
| GalNAcα1-3(Fucα1-2)-Galβ1-4Glc-AMC | A | — | 0.5 U/mg | 0.4 U/mg |
| GalNAcα1-3(Fucα1-2)-Galβ1-3GalNAcα1-3(Fucα1-2)-Galβ1-4Glc-AMC | A | — | 0.5 U/mg | 0.4 U/mg |

[1]Specific activities were determined as described under Examples using assays with approximately 50% and 100% final conversion of substrates evaluated at three time points (20, 40 and 60 min).

The specific activity of recombinant coffee bean α-galactosidase expressed in yeast and purified to homogeneity showed 32 U/mg with Galα1-pNP (at optimum pH 6.5). However, the specific activity of recombinant coffee bean α-galactosidase was only 17 mU/mg (approximately 2000 fold less) when measured with a blood group B tetrasaccharide-AMC substrate at the optimal pH used for enzymatic conversion of red cells with this enzyme (pH 5.5) (Table III).

Similarly, recombinant α-N-acetylgalactosaminidases from chicken liver revealed a strong preference for non-blood group A structures with highest activity measured with the non-natural substrate GalNAcα1-pNP. The specific activity of recombinant chicken α-N-acetylgalactosaminidase expressed in yeast and purified to homogeneity showed approximately 50 U/mg with GalNAcα1-pNP at the optimal pH of 3.65 (Table II), while only 0.3 U/mg (166 fold less) was measured with a blood group A tetrasaccharide-AMC substrate at pH 3.65 (Table III). The specific activity at pH 5.5 was lower at only 0.2 U/mg.

Similar results were found for the *Acremonium* sp., and *Patella vulgata* α-N-acetylgalactosaminidases (not shown).

(ii) $K_m$ for Different Substrates.

Reported Michaelis-Menton constants $K_m$ and $V_{max}$ (determined from Lineweaver-Burk plots) of the coffee bean α-galactosidase and the chicken liver α-N-acetylgalactosaminidase with different substrates are shown in Table IV.

TABLE IV

Apparent $K_m$ and $V_{max}$ of α-galactosidases and α-N-acetylgalactosaminidases with monosaccharide derivatives.

| Substrate Structure (derivative) | Recombinant coffee bean α-galactosidase pH 5.5, 26° C. | | Glycine Max. α-galactosidase pH 5.6, 26° C. | | Recombinant Chicken Liver α-N-acetylgalactosaminidase pH 3.65, 37° C. | |
|---|---|---|---|---|---|---|
| | $K_m$ | $V_{max}$ | $K_m$ | $V_{max}$ | $K_m$ | $V_{max}$ |
| Galα1-pNP | 363 μM[1] | 46.9 U/mg[1] | n.d[2] | n.d[2] | — | — |
| GalNAcα1-pNP | — | — | — | — | 827 μM[3] | 60.9 U/mg[3] |

[1]Zhu et al., (1995) *Arch Biochem Biophys* 324: 65-70, [2]Vosnidou et al., *Biochem Mol Biol Int* 46(1): 175-186, 1998, [3]Zhu et al., (1996) *Protein Exp and Purification* 8: 456-462.
Designation: n.d., not determined.

In the present invention similar $K_m$ values were obtained for recombinant purified coffee bean α-galactosidase and the chicken liver α-N-acetylgalactosaminidase. These $K_m$ values are relatively high and enzymes with 10 to 100 fold lower $K_m$ would represent preferred candidates for red cell conversions as near complete removal of antigens is predicted to be important.

Thus, the observed high $K_m$'s of these enzymes with all substrates appears to represent another reason for the poor performance of these enzymes in conversion of red cells.

An α-N-acetylgalactosaminidase isolated to apparent homogeneity from *R. torgues* was reported to have a specific activity of 50 U/mg with GalNAcα-pNP and a Km of 2-8 mM (Hoskins et al., *J Biol. Chem.* 272(12): 7932-9, 1997). Although, this enzyme appear to have a neutral pH optimum studies so far has not been able to demonstrate efficient enzymatic conversion of group A cells (Hoskins et al., Transfusion. 41(7): 908-16, 2001). It is likely that the poor performance of this enzyme is linked to the extremely high $K_m$.

(iii) pH Optima for Different Substrates.

Figure 1:
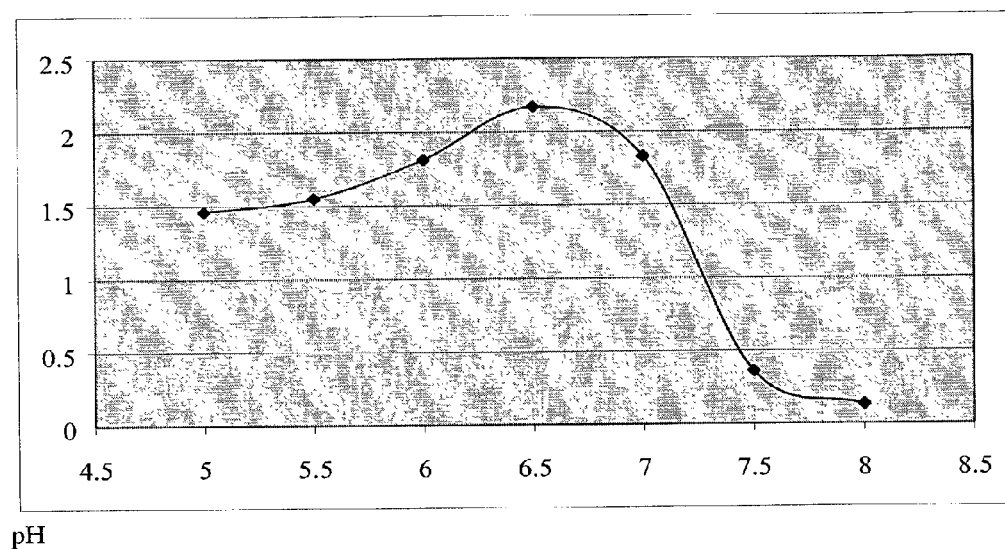
FIG. 1 illustrates the activity of recombinant coffee bean α-galactosidase with Galα-pNP at different pH. Assays were performed in reaction volumes of 0.5 ml containing 1.25 μmoles (2.5 mM) substrate. Reactions were incubated 20 min at 26° C., and quenched by addition of an equal volume of 0.2 M sodium borate buffer (pH 9.8). Release of p-nitrophenyl was quantified at OD 405 nm and plotted against pH. Buffers used: pH 5.0 and 5.5: 20 mM NaOAc; pH 6.0-8.0: 20 mM $NaPO_4$.
Figure 2:
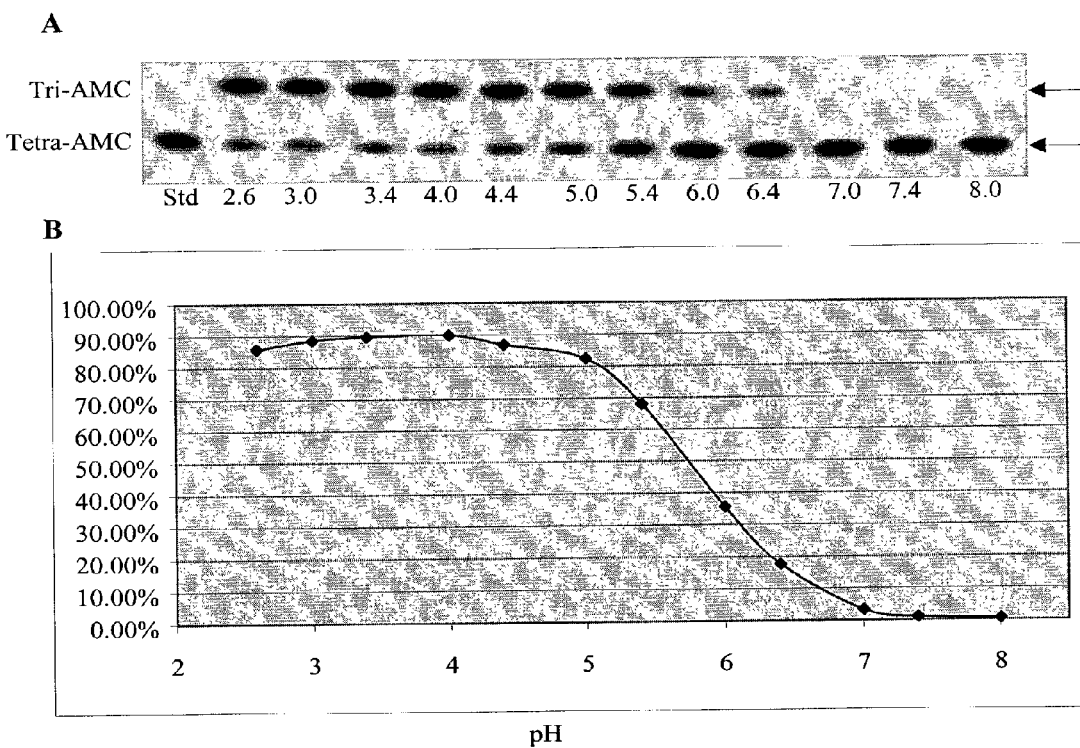
FIG. 2 illustrates the activity of recombinant coffee bean α-galactosidase with the blood group B tetrasaccharide AMC substrate at different pH. Assays were performed in reaction volumes of 10 μl containing 1 nmole of substrate in Na Citrate-$NaPO_4$ buffers, pH 2.6-7.4 and Na $PO_4$ buffer, pH 8.0. Reactions were incubated 40 min at 26° C., 3 μl of the reaction mixture was spotted onto HPTLC and developed in $CHCl_3$: methanol: $H_2O$ (60:35:8) and photographed. Panel A depicts the HPTLC analysis, Std indicates migration of substrate without enzyme; Panel B depicts the substrate cleavage quantified by scanning and plotted against pH.
Figure 3:
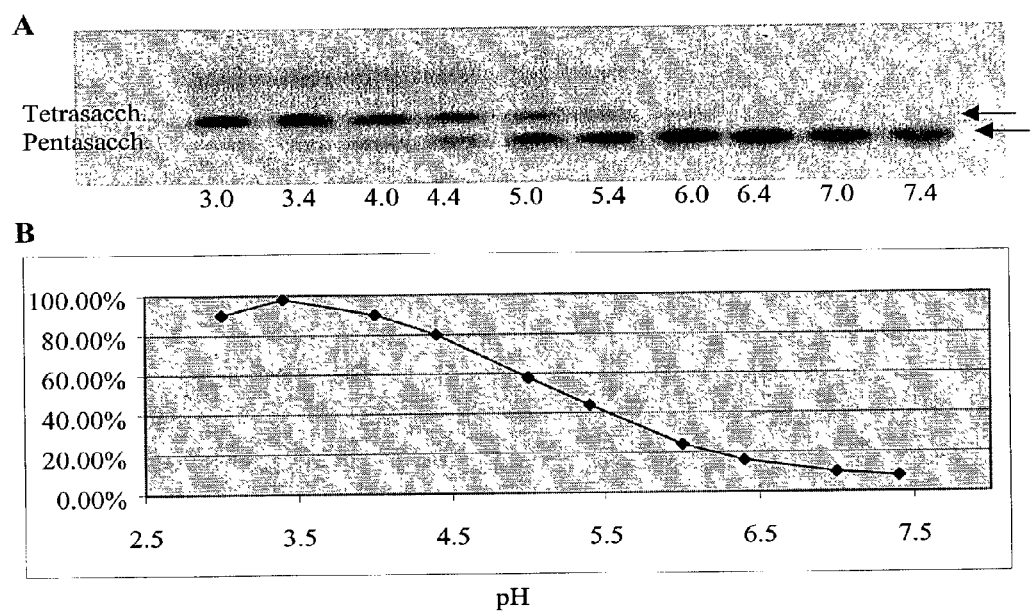
FIG. 3 illustrates the activity of recombinant coffee bean α-galactosidase with the Galili pentasaccharide substrate at different pH. Assays were performed in reaction volumes of 10 μl containing 5 nmoles of substrate in Na Citrate-$NaPO_4$ buffers. Reactions were incubated 20 min at 26° C., 2 μl of each reaction mixture was spotted onto HPTLC and developed in $CHCl_3$: methanol: $H_2O$ (30:60:20) and visualized by orcinol spray. Panel A depicts the HPTLC analysis; Panel B depicts the substrate cleavage quantified by scanning and plotted against pH.

The pH optima of coffee bean and *Glycine max* α-galactosidases have been reported to be broad and include neutral pH. Assays to measure pH optima were performed with the simple artificial α-Gal monoaccharide p-nitrophenyl derivative. Nevertheless, neither of these enzymes performs in blood cell conversions at neutral pH and conversions have only successfully been obtained at pH 5.5 to 6.4 (see discussion above). In order to provide insight into this phenomenon, we analyzed the pH optimum of the coffee bean enzyme with the p-nitrophenyl galactose and the oligosaccharide substrates B tetrasaccharide and the Galili pentasaccharide. As shown in FIG. 1, the pH optimum with the simple monosaccharide substrate was as reported previously broad with maximum activity at 6.4. In contrast, the pH optimum with the B tetrasaccharide substrate was acidic with maximum at 3.5 to 5.0 as shown in FIG. 2. Furthermore, a similar low pH optimum was found for the cleavage of the Galili oligosaccharide as shown in FIG. 3.

The optimal pH with of the coffee bean enzyme with melibiose, raffinose, and stachyose has been reported to be low (between 3.6-4) (Zhu et al., (1995) *Arch Biochem Biophys* 324: 65-70, Courtois and Petek (1966) *Methods Enzymol* 3: 565-571). This is in agreement with our findings for the B and Galili Oligosaccharides, and suggests that the enzyme generally have a low pH optimum with natural disaccharides and oligosaccharides.

It is likely that the pH optimum of the enzyme with the p-nitrophenyl substrate is artificial and linked to the physical properties of the aglycan rather than reflecting the properties of the enzyme with natural substrates. The data presented here therefore may provide an explanation for the failure of this enzyme to perform in red cell conversion at neutral pH.

The chicken liver α-N-acetylgalactosaminidase was reported to have pH optimum at 3.65 using GalNAcα-pNP as described above. Analysis of the influence of pH on this enzymes activity with the blood group A tetrasaccharide AMC substrate was in agreement with the reported data and showed a pH optimum of 3.5-4.5 (not shown).

As described above the chicken liver α-N-acetylgalactosaminidase and coffee bean α-galactosidase enzymes are members of a large homologous glycosidase gene family including the human lyzosomal enzymes. Lyzosomal enzymes generally function at acidic pH and all of these have been reported to have acidic pH optima. It is therefore likely that other homologous enzymes with sequence similarities to this group share this characteristic feature of an acidic pH optimum. We therefore chose to screen new sources for α-N-acetylgalactosaminidase and α-galactosidase activities using the appropriate substrates and neutral pH.

Example 2

Identification of α-N-Acetylgalactosaminidases and α-Galactosidases with Highly Preferential or Exclusive Substrate Specificity for the Blood Group A and/or B Blood Group Structures at Neutral pH In order to identify potential enzymes with preferred and/or exclusive specificity for blood group A and B structures, a large panel of fungal and bacterial isolates were analyzed. A protocol for initial screening with the blood group A/B tetrasaccharide AMC derivatives as well as the Gal/GalNAcα-pNP derivatives was developed. Briefly, preserved frozen stocks of cultures were inoculated onto YM slant cultures (tube size: 1.8×18 cm), grown at 27° C. for 8 days, and the cultures (spores) harvested by washing down with 5 ml cryogen (10% glycerol+5% lactose), followed by maceration (strongly whirling with glass beads in the screwed tube, 1.3× 13 cm). One ml of the slant cultures were inoculated to appropriate specific media for aerobic fermentation (25° C. for fungal cultivation and 28° C. for actinomycete cultivation) for 72~96 hours. Samples of 2.5 ml of each grown cultures were macerated in a screwed tube (1.3×13 cm) containing about 8-10 glass beads (size=3 mm diameter) by vortexing for 15 minutes, after which the pH was adjusted to 6.5 with citrate buffer and the macerated cultures frozen in tubes at −20° C. Frozen cultures were thawed and macerated again as above and centrifuged at 2100×g for 15 minutes. The supernatants served as enzyme source for the initial assay. Samples of 10 μl were tested as follows:

Assays with Group A or B Tetrasaccharide AMC Substrates:

Reaction mixtures of 10 μl containing 50 mM sodium citrate (pH 6.5), 0.25 nmol oligosaccharide AMC substrate, and 10 μl enzyme source as described above were incubated at 30° C., and product development was monitored at different time intervals (20 min to 48 hours) by HPTLC.

Assays with P-Nitrophenyl Monosaccharide Substrates:

Reaction mixtures of 20 μl containing 50 mM sodium citrate (pH 6.5), 2-5 mM monosaccharide pNP substrate and 10 μl enzyme source as described above were incubated at 30° C., and product development was monitored at different time intervals (20 min to 24 hours) by OD405 nm or HPTLC.

Screen for α-Galactosidase Activities:

A total of 2400 isolates were screened and five strains with significant activities with the group B tetrasaccharide AMC substrate were identified. These strains were selected for a small scale fermentation, which was processed by French press, $(NH_4)_2SO_4$ precipitation, and separation on Q-Sepharose. Further analysis of the pooled peaks of activity found in Q-Sepharose fractions revealed specific activities with the two substrates as listed in (Table VI).

TABLE VI

Substrate Specificity of Five Identified *Streptomyces* α-Galactosidase Activities.

| Enzyme Source | Specific activities of Q-Sepharose peak fractions[1] U/mg | |
|---|---|---|
| (Strain) | Galα1-pNP | Galα1-3(Fucα1-2)Galβ1-4GlcNAc-AMC |
| Strain #2075 | <0.02 | 0.004 |
| strain #2110 | <0.03 | 0.0007 |
| Strain #2260 | 0.0009 | <0.00003 |

TABLE VI-continued

Substrate Specificity of Five Identified *Streptomyces* α-Galactosidase Activities.

| Enzyme Source (Strain) | Specific activities of Q-Sepharose peak fractions[1] U/mg | |
|---|---|---|
| | Galα1-pNP | Galα1-3(Fucα1-2)Galβ1-4GlcNAc-AMC |
| Strain #2357 | n.d. | 0.075 |
| Strain #2371 | <0.005 | 0.0001 |

[1]Analysis of specific activities were determined in pooled active fractions from Q-sepharose chromatography. Purification was done from 60 ml of broth with protease inhibitors (PMSF, leupeptin, pepstain, EDTA) subjected to French pressing at 10,000 psi. This preparation was centrifuged at 13,000 x g for 30 minutes, and supernatant fractionated by ammonium sulfate precipitation at 15% and 50%. The 15-50% pellet was dissolved in 20 mM Tris (pH. 7.5), and filtered through a 0.45 μm filter. The clarified filtrate was loaded onto a 5 ml Pharmacia H-trap Q column and the proteins were eluted with a 0-0.15M NaCl gradient. Designation: n.d., not determined.

Figure 4:
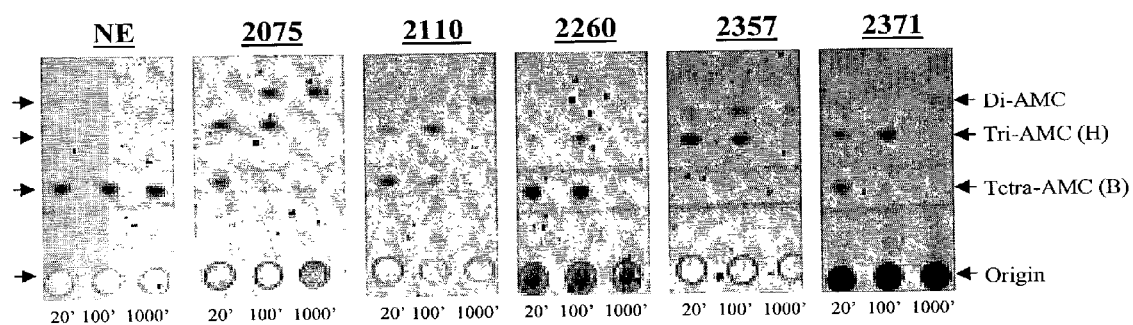
FIG. 4 is an HPTLC analysis of five selected Streptomycete α-galactosidase activities with the B tetrasaccharide AMC substrate. Designated strain numbers are the same as in Table V. The assay was performed as a time course with time points 20, 100 and 1000 min assessed by HPTLC. Migration of standard disaccharide, trisaccharide (H), and tetrasaccharide (B) AMC derivatives is indicated by arrows. NE, no enzyme control; Origin, sample application position. The appearance of a disaccharide AMC product most pronounced in #2075 is due to contaminating α-fucosidase activity.

The HPTLC analysis with group B tetrasaccharide AMC substrate of the five candidate strains is shown in FIG. 4. The activities of the five strains cleaved the B tetrasaccharide AMC substrate with varying degree to a product migrating as H trisaccharide AMC as well as in some cases to a disaccharide AMC derivative. The latter is due to contaminating α-fucosidase activity.

Strains 2075 and 2357 expressed highest activities with the B tetrasaccharide substrate. Activities with the αGal p-nitrophenyl substrate did not correlate with the activities with the B tetrasaccharide substrate. During purification, it was further confirmed that the two activities could be separated indicating that they were derived from different proteins. Only strain 2357 completely lacked activity with the αGal p-nitrophenyl substrate, which made further analysis simpler and this activity was chosen for further purification and characterization. A small scale fermentation of #2357 was performed and the enzyme activity was found in the soluble fraction after French press (See Table VI legend).

Serotyping of strain #2357 by colony morphology was performed by Accugenix, Newark, Del., confirming it as an actinomycete. Genotyping by Short Tandem Repeats of 500 base pairs placed strain #2357 in the Genus of *Streptomyces griseoplanus* with 1.60% difference.

Screen for α-N-acetylgalactosaminidase Activities:

A total of four strains with significant activities with the group A tetrasaccharide AMC substrate were identified (Table IV).

TABLE VII

Substrate Specificity of Four Identified *Streptomyces* α-N-acetylgalactosaminidase Activities.

| Enzyme Source (Strain | Specific activities of Q-Sepharose peak fractions[1] U/mg | | |
|---|---|---|---|
| | GalNAcα1-pNP | GalNAcα1-3(Fucα1-2)Galβ1-3GalNAc-AMC | GalNAcα1-3(Fucα1-2)Galβ1-3GalNAcα1-3(Fucα1-2)Galβ1-4GlcNAc-AMC |
| Strain 8 | n.d. | 0.0037 | 0.0037 |
| Strain 1488 | <0.00005 | 0.016 | 0.016 |
| Strain 1647 | n.d. | 0.0055 | 0.0055 |
| Strain 2233 | <0.00005 | 0.00028 | 0.00028 |

[1]Purification and assay as described in legend to Table VI.

Figure 5:
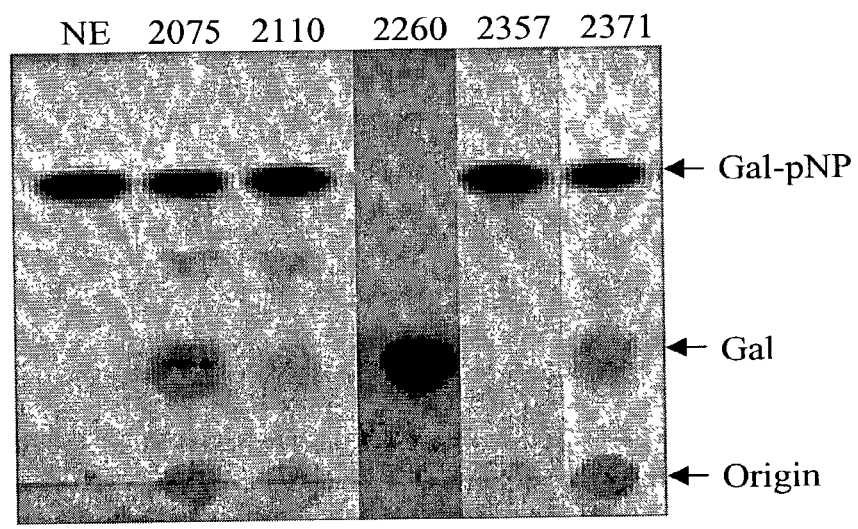
FIG. 5 is an HPTLC analysis of five selected Streptomycete α-galactosidase activities with Galα-pNP substrate. Assays were performed for 4 days at 30° C. Only strain #2260 showed significant activity with the pNP substrate, and no galactose release at all was detected in the extract of strain #2357.
Figure 5B:
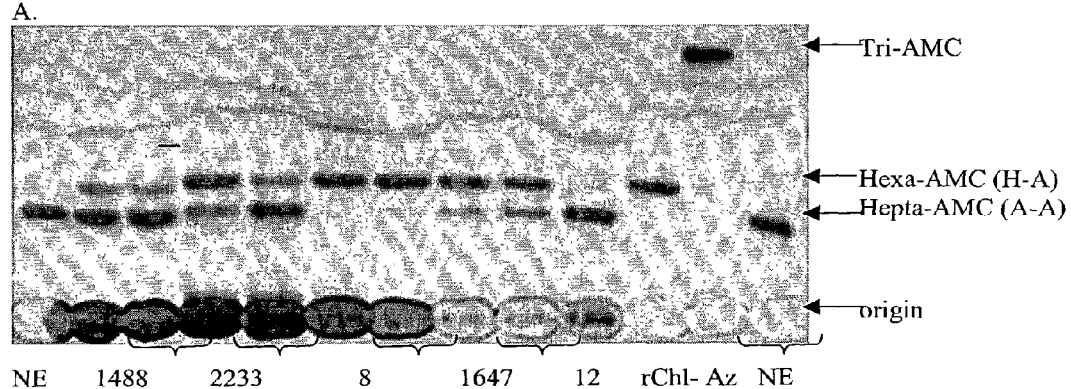
FIG. 5b is an HPTLC analysis of five selected Streptomycete α-N-acetylgalactosaminidase activities with the blood group A tetrasaccharide (Panel A) and A heptasaccharide AMC (Panel B) substrate. Streptomycete strains identified by numbers as in Table VII. Assays were performed in reactions of 10 µl containing 1 nmole of AMC-substrates, 5.0 µl of selected fractions of the enzyme, and the buffer 0.05M Na Citrate pH 6.0. Reactions were incubated 180 min at 30° C., and 2.5 µl of the reaction mixture was spotted onto HPTLC and developed in $CHCl_3$: methanol: $H_2O$ (60:35:8) and photographed. Migration of trisaccharide (H), and tetrasaccharide (A), heptasaccharide and hexasaccharide (H-A) AMC derivatives is indicated by arrows. NE, no enzyme control; rCHl-Az, recombinant Chicken liver A-zyme; Origin, sample application position. The appearance of a disaccharide AMC is due to contaminating α-fucosidase activity.
Figure 5B:
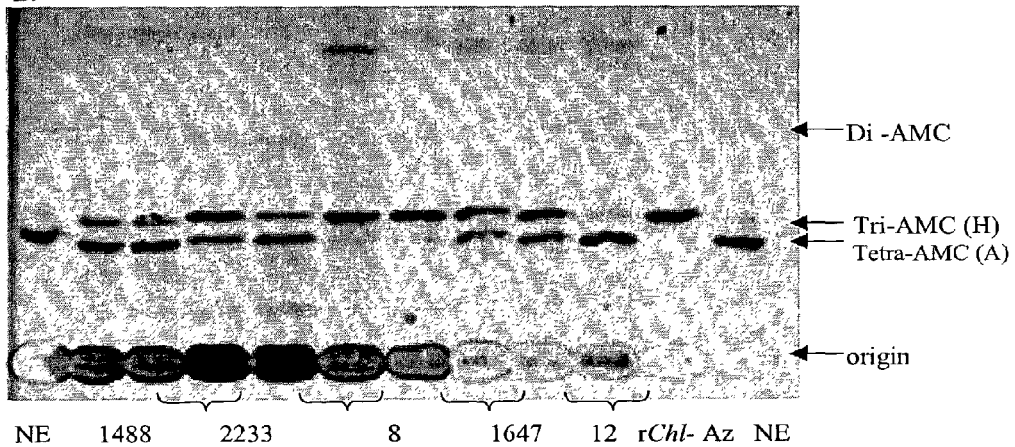

The HPTLC analysis with group A tetrasaccharide AMC substrate of the four candidate strains is shown in FIG. 5b.

All identified strains with significant activities with the A tetrasaccharide substrate showed none or barely detectable levels of activities with the p-nitrophenyl derivative.

Strains 8, 1488, and 1647 expressed the highest activities with the A tetrasaccharide substrate, but only the activity in #8 was stable and could be recovered for further characterization. This isolate was chosen for further analysis. A small fermentation was performed and the enzyme activity found to be insoluble and associated with the pelleted fraction after French press.

Serotyping of strain #8 by colony morphology was performed by Accugenix, Newark, Del., confirming it as an actinomycete. Genotyping by Short Tandem Repeats of 500 base pairs placed strain #8 in the Genus of *Streptomyces chattanoogensis* with 0.00% difference.

The above data showed that bacteria contain α-galactosidase and α-N acetylgalactosaminidase exoglycosidases with unique substrate specificities for the immunodominant αGalNAc or αGal residues of the complex blood group A and B antigens. Such enzymes are proposed to be preferred for use in enzymatic blood cell conversions due to their highly preferred or exclusive specificities for the substrate as found on red cells.

Example 3

Figure 6:
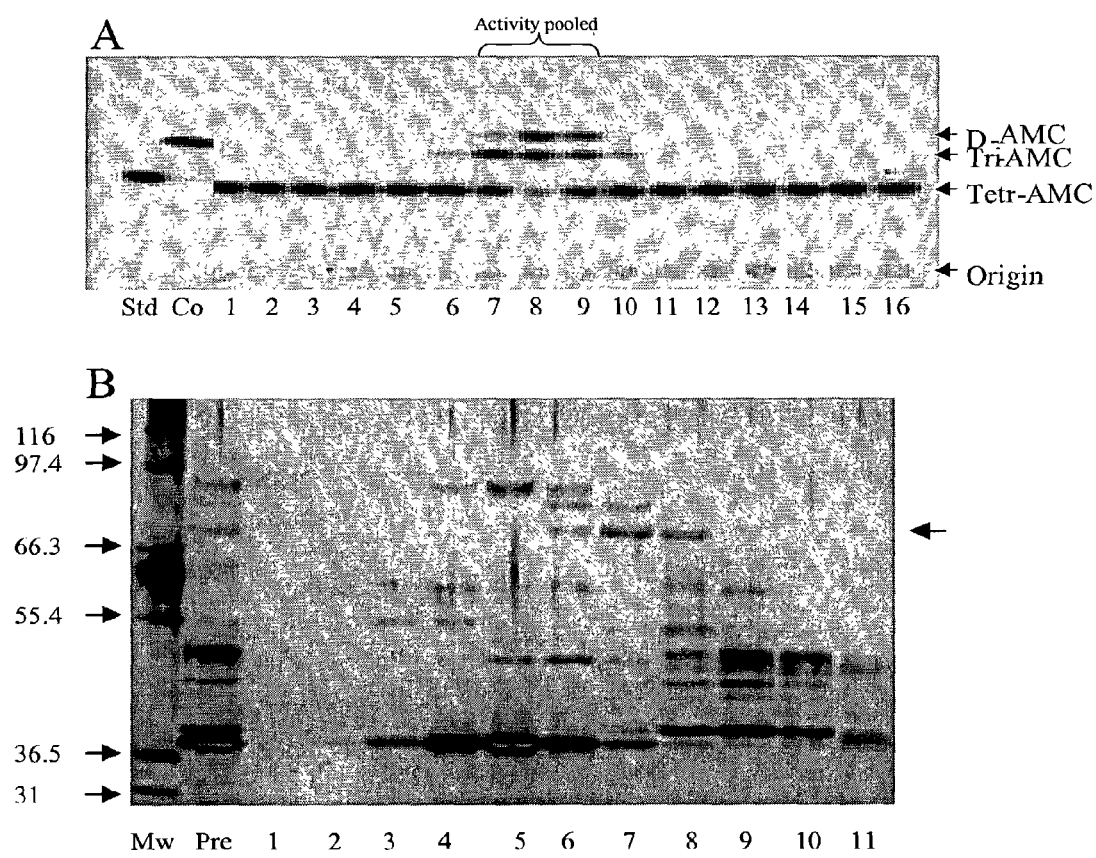
FIG. 6 is an Analysis of Streptomycete #2357 α-galactosidase enzyme separated by S12 chromatography. Pre: sample before chromatography. Panel A: HPTLC analysis of activity with the B tetrasaccharide AMC substrate. Reactions were performed in volumes of 10 µl containing 1 nmole substrate, 2 µl of the indicated S12 fractions, in 50 mM sodium citrate (pH 6.0) at 30° C. for 80 minutes. HPTLC was performed with 2.5 µl and developed with $CHCl_3$: methanol: $H_2O$ (60:35:8), dried and photographed. The peak activity area containing contaminating α-fucosidase activity in fractions 7-9 were pooled. Designations: Std, B tetrasaccharide AMC substrate without enzyme; Co, control reaction with coffee bean α-galactosidase. Panel B: SDS-NuPAGE analysis of fractions. Designations as in Panel A.

Isolation and Characterization of a Novel α-Galactosidase Identified from *Streptomyces* Strain #2357, which has Exclusive Substrate Specificity for the Branched Blood Group B Antigens and with Unprecedented High Specific Activity with Such Substrates A 20-liter fermentation culture was processed by the French press method. The main α-galactosidase activity was determined to be present in the supernatant after centrifugation at 10,000×g. The supernatant was fractionated by ammonium sulfate precipitation and approximately 70% activity was found in the 20-60% fraction. The precipitate of the 20-60% cut was dissolved in 20 mM Tris (pH 7.5) and clarified by centrifugation. The supernatant was sequentially fractionated by chromatography on Q-sepharose (buffer 20 mM Tris, pH 7.5, with a gradient of 0-1.5 M NaCl), S-sepharose (buffer 20 mM NaOAc, pH 5.3, with a gradient of 0-1.0 M NaCl), and by S12 gel filtration chromatography (buffer 20 mM NaOAc, pH 5.3, with 0.5 M NaCl or 20 mM NaPO$_4$, pH 6.5, with 0.5 M NaCl). Enzyme activity with the B tetrasaccharide AMC substrate was monitored in fractions collected throughout this purification scheme. Lack of activity with the Galα-pNP was confirmed throughout the separation steps. The final purified enzyme activity was recovered in fractions of the S12 chromatography eluting corresponding to a molecular weight of approximately 70,000 similar to the elution of bovine serum albumin run as a standard (FIG. 6, panel A). SDS-NuPAGE analysis of the S12 chromatography fractions revealed multiple bands in fractions containing α-galactosidase activity, but the fraction with peak activity only contained a few bands migrating in the region of 40-80 kD (FIG. 6, panel B).

Figure 9:
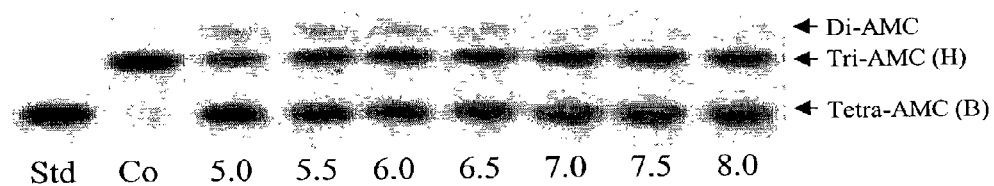
FIG. 9 illustrates the activity of purified α-galactosidase from #2357 with the blood group B tetrasaccharide AMC substrate at different pH. Assays were performed in reaction volumes of 10 µl containing 1 nmole of substrate in 20 mM NaOAc (pH 5.0-5.5) or $NaPO_4$ (pH 6.0-8.0). Reactions were incubated 40 min at 26° C., 3 µl of the reaction mixture was spotted onto HPTLC and developed in $CHCl_3$: methanol: $H_2O$ (60:35:8) and photographed. Panel A: HPTLC analysis, Std indicates migration of substrate without enzyme; Panel B: Substrate cleavage quantified by scanning and plotted against pH.
Figure 9:
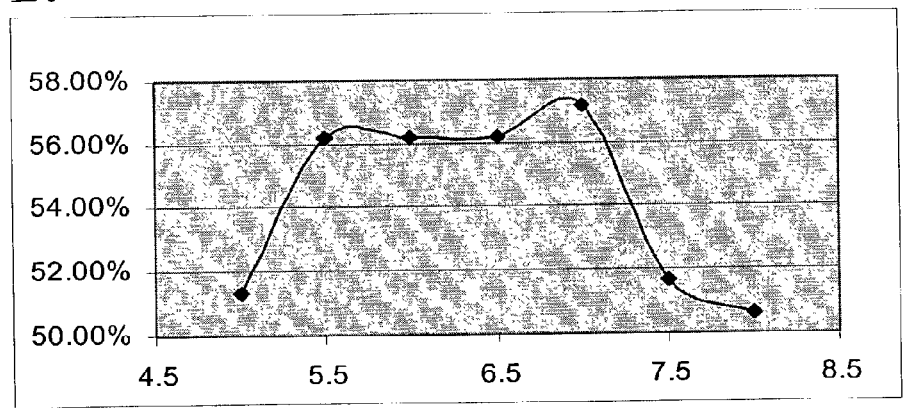
Figure 9B:
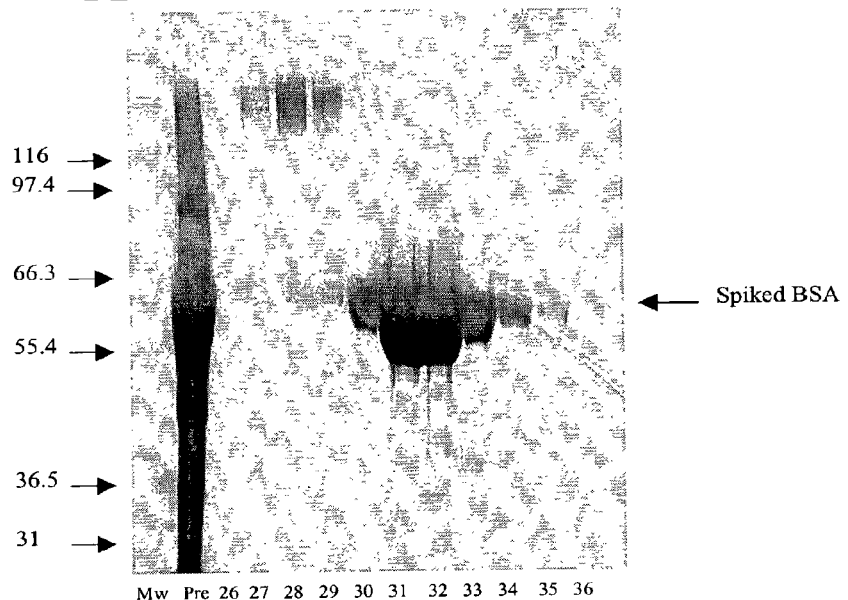
FIG. 9B illustrates analysis of purified α-galactosidase from #2357 spiked with BSA separated by S12 chromatography. Panel A: SDS-NuPAGE analysis of fractions 26-36. Designations: Mw: molecular weight markers; Pre: sample before chromatography. Panel B: HPTLC analysis of activity with the B tetrasaccharide AMC substrate. Reactions were performed in volumes of 10 µl containing 1 nmole substrate, 2 µl of the indicated S12 fractions, in 50 mM $NaPO_4$, pH 7.0. HPTLC was performed with 2 µl and developed with $CHCl_3$: methanol: $H_2O$ (60:35:8), dried and photographed. Designations: Std, B tetrasaccharide AMC substrate without enzyme; Co, control reaction with coffee bean α-galactosidase; D-AMC, disaccharide-AMC; Tri-AMC, trisaccharide-AMC; Tetr-AMC; tetrasaccharide-AMC.
Figure 9B:
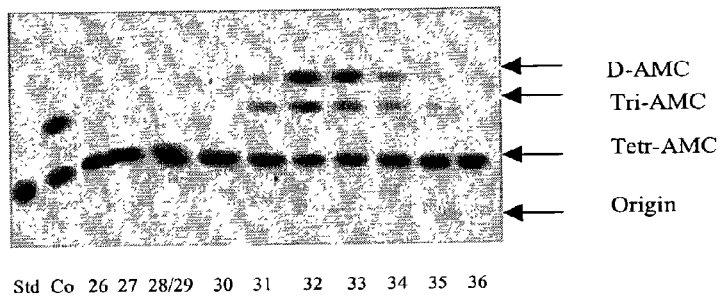

The specific activity of the pooled enzyme peak from the last S12 chromatography step was approximately 10 U/mg (protein determined by silver staining of SDS-NuPAGE and comparing the desired protein band with the amount of protein in the protein bands in the molecular weight marker). Comparing the elution of activity with that of bovine serum albumin revealed that the activity eluted after BSA, which provides evidence that the active protein has a molecular size lower than BSA, i.e. lower than 65 kd, as evaluated by gel filtration chromatography (FIG. 9b).

Figure 7:
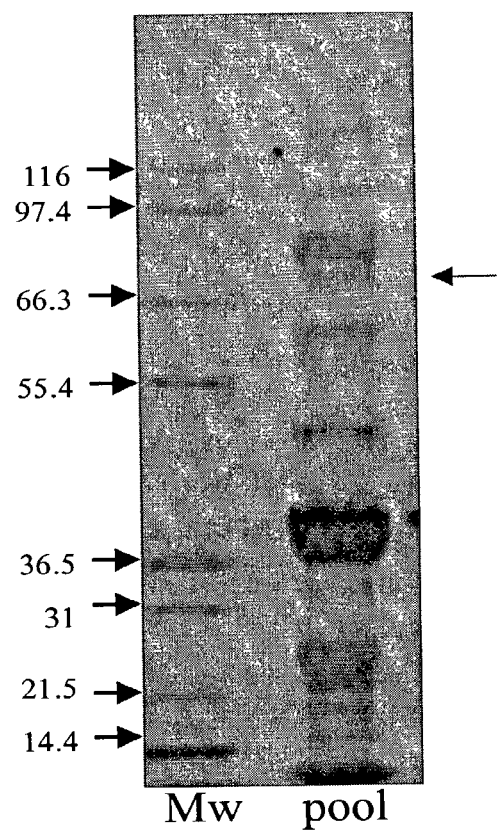
FIG. 7 is an SDS-NuPAGE of pooled fractions from S12 chromatography of enzyme activity purified from #2357. R-250 stained PVDF membrane of SDS-NuPAGE. The protein band excised for sequencing is indicated by an arrow.

The pooled fractions from the S12 chromatography containing the peak activity were further purified by reverse phase chromatography using a C4 column (BioRad) (buffer: 0.1% TFA with a gradient of 0-100% acetonitrile). Eluted proteins were analyzed by SDS-NuPAGE and the fractions contained most of the desired protein band migrating at 70 kD were pooled and dried under vacuum. The pooled fraction was rerun on SDS-NuPAGE and blotted onto PVDF membrane and stained with R-250 (FIG. 7). The desired protein band was excised and subjected to N-terminal sequencing using Applied Biosystems Model 494 Precise Protein Sequencer w/Model 140C Microgradient Delivery System and Model 785A Programmable Absorbance Detector. A single short sequence was obtained:

(SEQ ID NO: 1)
Phe-Ala-Asn-Gly-Leu-Leu-Leu-Thr.

Since the isolated α-galactosidase activity was not purified to homogeneity it is possible that the obtained sequence originates from another protein. Further purification is required to isolate and characterize the novel enzyme protein and the encoding gene, and this is in progress.

Figure 8:
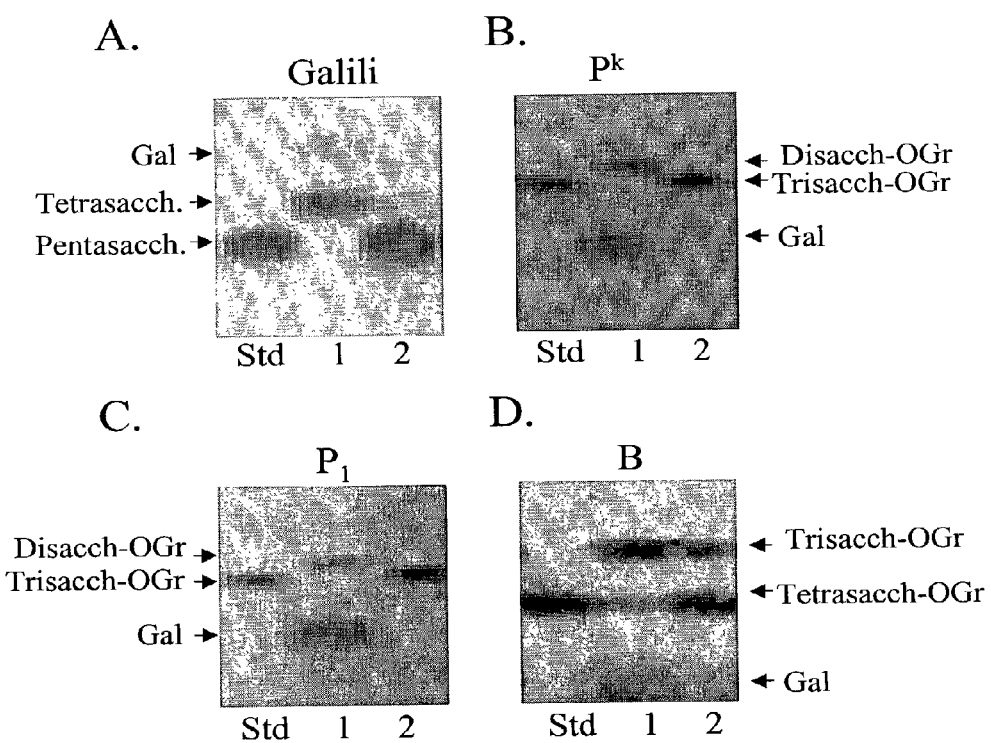
FIG. 8 is an HPTLC analysis of substrate specificities of recombinant coffee bean α-galactosidase and purified α-galactosidase from #2357. The coffee bean α-galactosidase (lanes 1) efficiently cleaved all substrates tested, while the purified α-galactosidase from #2357 selectively only cleaved the blood group B tetrasaccharide. Panel A: Galili substrate (Galα1-3Galβ1-4GlcNAcβ1-3Galβ1-4Glc); Panel B: $P^k$ substrate (Galα1-3Galβ1-4Glc-OGr); Panel C: $P_1$ substrate (Galα1-3Galβ1-4GlcNAc-OGr); and Panel D: B substrate (Galα1-3[Fucα1-2]Galβ1-4GlcNAcβ-OGr. HPTLC in Panels A, B and C were developed using $CHCl_3$: methanol: $H_2O$ (60:35:8), and Panel D in $CHCl_3$: methanol: $H_2O$ (30:60:10).

Nevertheless, the novel α-galactosidase activity was highly purified and had a specific, activity of over 10 U/mg with the B tetrasaccharide. The enzyme preparation allowed detailed studies of the substrate specificity and kinetic properties of the novel enzyme. The substrate specificity of the purified #2357 α-galactosidase was characterized using a large panel of oligosaccharides and derivatives with terminal α-Gal residues. The assay was performed as described above using 1-4 nmoles substrate and the amount of enzyme required to cleave this amount of the B tetrasaccharide AMC structure in 60 min. HPTLC analysis was performed at different time points. An example of the analysis is shown in FIG. 8. The substrate specificity of the purified #2357 α-galactosidase activity is summarized in Table VIII.

showed activity with all structures containing a terminal α-Gal residue. Both α1-3 (blood group B and the "Galili-epitope" without fucose) and α1-4 (blood group $P_1$ and $P^k$) were substrates and the length or branching of the oligosaccharide structure only had effect on relative activity, i.e., the quantities of enzymes required to reach completion (specific activities only determined for Galα p-nitrophenyl and B tetrasaccharide AMC).

In striking contrast the activity identified and purified from *Streptomyces* strain #2357 only exhibits activity with the blood group B structures when presented as a tetrasaccharide or longer. The inability of this enzyme to cleave p-nitrophenyl or methyl-umbrellifryl monosaccharide αGal derivatives showed that the lack of activity with monosaccharides are not simply due to the aglycan and conjugation. The trisaccharide structure, Galα1-3(Fucα1-2)Gal-AMC, was inactive which may be related to the conjugation chemistry as the corresponding structure, Galα1-3(Fucα1-2)Galβ-OGr, served as a substrate. Except for this the *Streptomyces* α-galactosidase efficiently utilized all the branched group B related structures, which represents all know B structures found on red cells (Table I). This is the first α-galactosidase exhibiting unique substrate specificity for the blood group B structures and showing no activity with the human blood group antigen $P_1$ as well as the rare antigen $P^k$. Thus, enzymatic conversion of red cells with the *Streptomyces* α-galactosidase will result in intact $P_1$ antigenicity in contrast to treatments with known α-galactosidases including the coffee bean α-galactosidase (Kruskall et al. *Transfusion* 2000; 40(11): 1290-8). Similarly, it is expected that the rare $P^k$ antigen will be intact after enzymatic conversion. Approximately 80% of caucasian population express the $P_1$ antigen on red cells and, although the function of this antigen is unknown, it is considered an important improvement in the enzymatic conversions to limit the removal of antigens solely to the A and B blood group antigens.

TABLE VIII

Substrate Specificity of α-Galactosidases

| Substrate Structure (derivative) | Blood Group Specificity | Recombinant Coffee Bean α-galactosidase | Purified *Streptomyces* #2357 α-galactosidase |
|---|---|---|---|
| Galα-Mu | — | +[1] | − |
| Galα-pNP | — | + | − |
| GalNAcα-pNP | — | − | − |
| Galα1-3Galβ-OGr | — | + | − |
| Galα1-4Gal | P | + | − |
| Galα1-4Galβ1-4GlcNAcβ-OGr | $P_1$ | + | − |
| Galα1-4Galβ1-4Glcβ-OGr | $P^k$ | + | − |
| Galα1-3(Fucα1-2)Galβ-OGr | B | + | + |
| Galα1-3(Fucα1-2)Gal-AMC | B | + | − |
| Galα1-3(Fucα1-2)Galβ1-3GlcNAcβ-OGr | B | + | + |
| Galα1-3(Fucα1-2)Galβ1-3GalNAcα-OGr | B | + | + |
| Galα1-3(Fucα1-2)Galβ1-3GalNAcβ-OGr | B | + | + |
| Galα1-3(Fucα1-2)Galβ1-4Glc-AMC | B | + | + |
| Galβ1-3GalNAcβ1-3Galβ1-4Glc-AMC | Tβ | − | − |
| GalNAcα1-3(Fucα1-2)Galβ1-4Glc-AMC | A | − | − |
| Galα1-3Galβ1-4GlcNAcβ1-3Galβ1-4Glc | Galili B | + | − |
| Galα1-3(Fucα1-2)Galβ1-3(Fucα1-4)GlcNAcβ-OGr | B | + | + |
| Galα1-3(Fucα1-2)Galβ1-4(Fucα1-4)GlcNAcβ-OGr | B | + | + |

[1]Designations: "+": Cleavage was detected within 60 minutes, "−": No cleavage was detected by overnight incubation. The linear trisaccharide as well as Galili B cleavage reactions were evaluated by HPTLC using $CHCl_3$:methanol:$H_2O$ (30:60:10). All other cleavage reactions were analyzed using $CHCl_3$:methanol:$H_2O$ (60:35:8).

For comparison recombinant coffee bean α-galactosidase was included in all analyses. In agreement with our studies described in Example 1, the coffee bean α-galactosidase The pH optimum of the purified *Streptomyces* α-galactosidase was analyzed as shown in FIG. 9. The enzyme activity with B tetrasaccharide AMC substrate had a broad pH optimum around 5.5-7.0. This enzyme therefore is expected to perform in red cell conversions at neutral pH in contrast to enzymes used in the past.

This is the first α-galactosidase or α-N-acetylgalactosaminidase activity identified that have exclusive or even preferred substrate specificity for the blood group B or A structures over simple monosaccharide derivatives. The α-galactosidase enzyme has a specific activity with the blood group B structures higher than 10 U/mg, which is more than 500 fold higher than that measured for the coffee bean α-galactosidase, as described in Example 1. Although this information is not available for all other identified and characterized α-galactosidases, it is likely that these show the same poor properties as the coffee bean α-galactosidase, because they generally function efficiently with the αGal p-nitrophenyl derivative and because the genes encoding these are homologous. The identified *Streptomyces* α-galactosidase in the present invention is therefore unique and without precedence in the prior art, and the kinetic properties identified for this enzyme holds great promise for performance in enzymatic B blood cell conversion.

Example 4

Characterization of Recombinant α-N-Acetylgalactosaminidase Expressed in *E. coli*

New England BioLabs Inc. has recently commercialized a recombinant α-N-acetylgalactosaminidase (catalog no. P0734B) disclosed to be expressed in *E. coli*. The enzyme is derived from a proprietary strain, and reportedly catalyzes the hydrolysis of terminal α-GalNAc linkages from oligosaccharides and αGalNAc p-nitrophenyl (New England BioLabs Inc. catalog information). In a screen of commercially available exo-glycosidases we found this α-N-acetylgalactosaminidase to partly exhibit the preferred characteristic of having a relative high specific activity with A tetra- and heptasaccharide AMC derivatives compared to αGalNAc monosaccharide derivatives (Table IX). Importantly, the absolute specific activity with the blood group A derivatives of this enzyme is not considerably different from that of, e.g., the chicken liver enzyme. However, the relative activity compared to the monosaccharide substrate is considerably different. Thus, the data suggests that the *E. coli* expressed α-N-acetylgalactosaminidase has a better relative specificity for the blood group A antigen.

TABLE IX

Specific activity of *E. coli* expressed a-N-acetylgalactosaminidase.

| Substrate Structure (derivative) | Blood Group Specificity | Recombinant α-N-acetylgalactosaminidase pH 5.5 | pH 7.0 |
|---|---|---|---|
| Galα1-pNP | — | — | — |
| GalNAcα1-pNP | — | 2.3 U/mg[1] | 2.5 U/mg |
| Galα1-3(Fucα1-2)Galβ1-4GlcNAcβ-AMC | B | — | — |
| GalNAcα1-3(Fucα1-2)Galβ1-3GalNAcβ-AMC | A | 0.27 U/mg | 0.27 U/mg |

TABLE IX-continued

Specific activity of *E. coli* expressed a-N-acetylgalactosaminidase.

| Substrate Structure (derivative) | Blood Group Specificity | Recombinant α-N-acetylgalactosaminidase pH 5.5 | pH 7.0 |
|---|---|---|---|
| GalNAcα1-3(Fucα1-2)Galβ1-3GalNAcα1-3(Fucα1-2)Galβ1-4GlcNAcβ-AMC | A | 0.26 U/mg | 0.27 U/mg |

[1]Assay conditions were as follows: Assays with p-nitrophenyl were done in reaction volumes of 0.5 ml containing 0.05 µmoles (100 µM), 50 mM sodium phosphate (pH 5.5 or 7.0), and 0.5 µg enzyme. Reactions were incubated 10 min at 37° C., and quenched by addition of an equal volume of 0.2M sodium borate buffer (pH 9.8). Assays with AMC substrates were done in reaction volumes of 10 µl containing 1 nmol substrate (100 µM), 50 mM sodium phosphate or 0.25M glycine (pH 5.5 or 7.0), and 0.05-0.1 µg enzyme. Reactions were incubated at 26° C. or 37° C. and analyzed by HPTLC at time points 0, 15, 30, and 60 min. Protein quantification was performed by semi-quantification using Coomassie stained SDS-PAGE analysis and weighed BSA as comparator.

Analysis of the fine substrate specificity of the *E. coli* expressed α-N-acetylgalactosaminidase revealed that it similarly to the chicken liver α-N-acetylgalactosaminidase utilized blood group A and repetitive A structures equally efficient (Table IX).

Further analysis with a panel of non-fucosylated oligosaccharide structures with terminal αGalNAc residues showed that the enzyme has approximately equal efficiency with these substrates compared to the group A branched substrates (Table X).

TABLE X

Substrate specificity of *E. coli* expressed α-N-acetylgalactosaminidase.

| Substrate Structure (derivative) | Blood Group Specificity | Recombinant α-N-acetylgalactosaminidase pH 6.0 and pH 7.0 |
|---|---|---|
| GalNAcα1-2Galβ1-OGr | — | +[1] |
| GalNAcα1-3Galβ1-4GlcNAcβ1-OGr | — | + |
| GalNAcα1-4Galβ1-4Glcβ1-OGr | — | + |
| GalNAcα1-3Galβ1-3GlcNAcβ1-OGr | — | + |
| GalNAcα1-3(Fucα-2)Galβ1-3GalNAcα1-OGr | A | + |

[1]Assays were performed in reaction mixtures of 10 µl containing 1-4 nmoles substrate (100-400 µM), 50 mM sodium citrate (pH 6.0), and 0.125 µg enzyme. Reactions were incubated at 31° C. and analyzed by HPTLC at time points 0, 30, 60 and 120 min.

Figure 10:
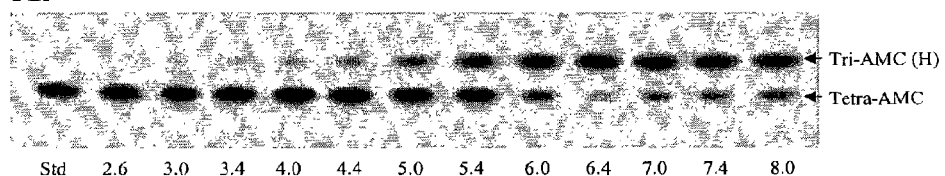
FIG. 10 illustrates the activity of E. coli expressed α-N-acetylgalactosaminidase with the blood group A tetrasaccharide AMC substrate at different pH. Assays were performed in reactions of 10 µl containing 1 nmole of A-tetra, 0.05 µg enzyme, and the buffer Na Citrate-$NaPO_4$ at varying pH 2.6-8.0. Reactions were incubated 40 min at 26° C., and 3 µl samples analyzed by HPTLC. Panel A: HPTLC analysis; Panel B: Substrate cleavage quantified by scanning and plotted against pH.
Figure 10:
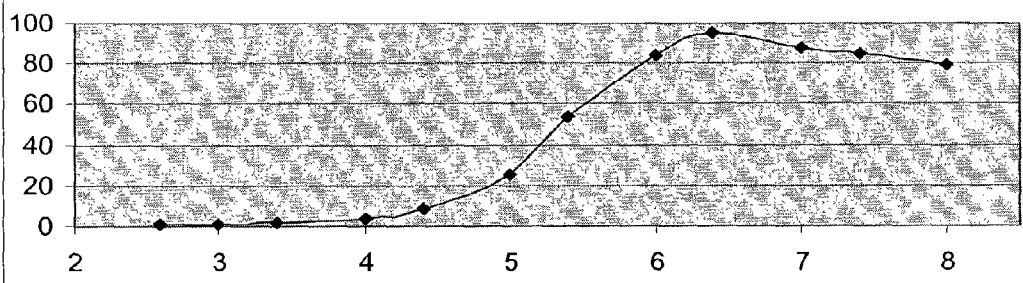

The *E. coli* expressed α-N-acetylgalactosaminidase exhibited a broad pH optimum including pH 6.0-7.0 with both monosaccharide and oligosaccharide substrates FIG. 10. At acidic pH below 5.5 the activity drops rapidly and at pH 4.4 and lower activity is hardly detectable. This is the first α-N-acetylgalactosaminidase identified with the preferred neutral pH optimum characteristic for red cell conversion.

The α-N-acetylgalactosaminidase activity was largely unaffected by buffer type: 50-250 mM glycine, 0.1 M glycylglycine, 20-50 mM sodium phosphate, 12.5-25.0 mM sodium citrate, 12.5-25.0 sodium citrate and 5.0-10.0 sodium phosphate, McIlvine solution pH 5.5, PBS, MES. The enzyme was also unaffected by NaCl (0-150 mM), glutathione and n-octyl-β-D-glucopyranoside.

Finally, evaluation of the kinetic constant $K_m$ for the monosaccharide derivative revealed that the enzyme has a significantly lower apparent $K_m$ (Table XI), as compared to the chicken liver α-N-acetylgalactosaminidase or the α-galactosidases described in Example 1 (Table IV).

TABLE XI

Apparent Km and $V_{max}$ of E. coli expressed a-N-acetylgalactosaminidase with monosaccharide derivatives.

| Substrate Structure (derivative) | Recombinant α-N-acetylgalactosaminidase pH 70, 37° C. | |
|---|---|---|
|  | $K_m$ | $V_{max}$ |
| Galα1-pNP | — | — |
| GalNAcα1-pNP | 10-50 μM | 3.3 U/mg[3] |

[1]Assay conditions were as follows: Assays with p-nitrophenyl were done in reaction volumes of 0.5 ml containing from 3.9-50 nmoles (1.5-100 μM) 50 mM sodium phosphate (pH 5.5 or 7.0), and 0.5 μg enzyme. Reactions were incubated 10 min at 37° C., and quenched by addition of an equal volume of 20 mM sodium borate buffer (pH 9.8). The amount of the liberated p-nitrophenol was determined by measuring the absorbance at 405 nm compared to a standard curve of p-nitrophenol. Michaelis-Menten constants $K_m$ and $V_{max}$ determined from Lineweaver-Burk plots.

TABLE XI-continued

Apparent Km and $V_{max}$ of E. coli expressed a-N-acetylgalactosaminidase with monosaccharide derivatives.

| Substrate Structure (derivative) | Recombinant α-N-acetylgalactosaminidase pH 70, 37° C. | |
|---|---|---|
|  | $K_m$ | $V_{max}$ |

[3]Zhu et al., (1996) Protein Exp and Purification 8: 456-462.

Furthermore, preliminary results indicate that the $K_m$ for the blood group A oligosaccharide substrates similarly is approximately 20 μM. The assay used for this determination involved densitometric scans of the substrate/product ratio using the tetrasaccharide AMC substrate (GalNAcα1-3 (Fucα1-2)Galβ1-4GalNAc-AMC). This assay is unreliable at low concentrations, and it is therefore possible that the $K_m$ is even lower than 20 μM.

In summary, the E. coli expressed α-N-acetylgalactosaminidase exhibits a relatively high preference for blood group A substrates, maximum activity with blood group A substrates at neutral pH, and favorable kinetic properties defined by a low $K_m$.

Example 5

Enzymatic Conversion of $A_1$ and $A_2$ Red Blood Cells to O Phenotype Cells Using E. coli Expressed α-N-Acetylgalactosaminidase, as Evaluated by Routine Typing Protocols Complete removal of the immunodominant A epitopes on human group A red cells have not previously been reported as described in detail above. Enzymatic conversion of blood group A cells of the weak subgroup $A_2$ have been reported using the chicken liver α-N-acetylgalactosaminidase at acidic pH, but the results of conversions were not verified by sensitive typing reagents and methods used in standard blood typing procedures. As detailed below in Table XII, initial attempts to improve the performance of the chicken liver α-N-acetylgalactosaminidase using different reaction conditions failed to produce completely converted cells. While reactivity with a monoclonal anti-A antibody from Dako could be abolished for $A_2$ cells, typing with more sensitive reagents clearly revealed that the enzymatic degradation of group A epitopes were incomplete.

TABLE XII

Conversion[1] of $A_1$ and $A_2$ red blood cells with recombinant chicken liver α-N-acetylgalactosaminidase

|  | Pre Enzyme Treatment | | | | Post Enzyme Treatment | | | |
|---|---|---|---|---|---|---|---|---|
|  | Ortho Anti-A | Dolichos biflorus | Ulex europaeus | Dako Anti-A | Ortho Anti-A | Dolichos biflorus | Ulex europaeus | Dako Anti-A |
| A1 Donor #1 | 4+ | 4+ | 0 | 3+ | 4+ | 0 | 4+ | 3+ |
| A1 Donor #2 | 4+ | 4+ | 0 | 4+ | 4+ | 0 | 4+ | w+ |
| A2 Donor #1 | 4+ |  |  |  | 4+ |  |  |  |
| A2 Donor #2 | 4+ | 0 | 3+ | 3+ | 4+ | 0 | 4+ | 1+ |
| A2 Donor #3 | 4+ | 0 | 4+ | 4+ | 4+ | 0 | 4+ | 0 |

[1]Protocols used for conversion with chicken α-N-acetylgalactosaminidase: Three conversion protocols were evaluated for conversion of $A_1$ and $A_2$ red cells with recombinant chicken liver α-N-acetylgalactosaminidase.

Conversion Protocol—A $A_2$ red cells (Beth Israel Deaconess Medical Center, Boston, Mass.) drawn in EDTA tubes and stored at 4° C. for up to seven days, were washed three times in PBS (Phosphate Buffered Saline, pH 7.4), and resuspended to 10% in a solution of PBS and 7.5% PEG (pH 7.4). Cells were treated with recombinant chicken liver α-N-acetylgalactosaminidase (100 U/ml) at 30° C. for 180 min while shaking. Cells were washed three times in 0.9% saline and resuspended to 3-5% in saline for typing.

Conversion Protocol—B $A_1$ red cells (Beth Israel Deaconess Medical Center, Boston, Mass.) drawn in EDTA tubes and leukoreduced $A_2$ red cells (American Red Cross, New England Region, Dedham, Mass.) were frozen in Glycerolyte57, (Baxter Healthcare Corporation, Fenwal Division: Deerfield, Ill.) according to the AABB Technical Manual, 13th edition, Method 6.6 and stored at −70° C. Prior to enzyme treatment cells were deglycerolized using 9.0% saline, 2.5% saline, and 0.9% saline (Method 125 of Immunohematology Methods by the American Red Cross was followed), resuspended to a hematocrit of 50% in a solution of PBS and 7.5% PEG (pH 7.4) and recombinant chicken liver α-N-acetylgalactosaminidase (200 U/ml) added. Reactions were incubated at 37° C. shaking for 4 hours, followed by three washes in 0.9% saline, and final suspension to 3-5% in saline for typing.
Conversion Protocol—C Origin and storage of cells same as described under protocol B. Deglycerolized red cells were washed twice in PCI (pH 5.5) with 150 mM NaCl and resuspended to a hematocrit of 50% in PCI (pH 5.5) with 150 mM NaCl. Cells were treated with recombinant chicken liver α-N-acetylgalactosaminidase (200 U/ml) at 37° C. shaking for 4 hours, followed by three washes in 0.9% saline, and final suspension to 3-5% in saline for typing.

It is evident from the data in Table XII that apparent removal of A antigens is achieved, when defined by one particular anti-blood group A specific monoclonal antibody that is not approved for blood typing procedures (DAKO). A large number of such antibodies exist and, due to specificity and low affinity binding, they are inappropriate for serological typing purposes. Development of monoclonal cocktails for ABO routine typing to substitute previously used polyclonal antibody reagents was a major achievement for the blood bank industry in 1990s. Analysis of removal of A antigens by these highly sensitive and approved routine typing reagents showed, in contrast to the DAKO, antibody that little conversion had occurred, as defined by agglutination titer. Details of the typing assay used in this example is as follows: Approved typing reagents used in hemagglutination assays were murine monoclonal antibodies and plant lectins obtained from Ortho Clinical Diagnostics, Raritan, N.J.; Gamma Biologicals/Immucor, Norcross, Ga. Non-approved reagents included murine monoclonal anti-A antibody from Dako and a panel of monoclonal antibodies to blood group A variants produced by H. Clausen (Clausen et al., Proc. Natl. Acad. Sci. USA 82(4): 1199-203, 1985, Clausen et al., J Biol. Chem. 261(3): 1380-7, 1986, Clausen et al., *Biochemistry* 25(22): 7075-85, 1986, Clausen et al., *J Biol. Chem.* 262(29): 14228-34, 1987). Typing reagents were used according to the manufacturers recommendations and other monoclonal antibodies as determined by titration.

Hemagglutination Assay (Room Temperature)
1. A 3-5% suspension of washed red cells in isotonic blood bank saline was prepared.
2. One drop (approx 50 μl) of antibody/lectin reagent was added.
3. One drop (approx 50 μl) of the red cell suspension was added
4. Tubes were mixed and centrifuged for 15 seconds at 3500 rpm.
5. Cells were resuspended by gentle agitation and examined macroscopically for agglutination.
6. The agglutination was graded according to Method 1.8 in the AABB Technical Manual, 13 edition.

Similar results were obtained with a purified fungal α-N-acetylgalactosaminidase from *acremonium* sp. (Calbiochem) (not shown).

As described in the previous examples, preferred enzymes for use in removing blood group A or B epitopes from red cells are likely to have particularly good kinetic properties with oligosaccharide substrates resembling the blood group A or B antigens. Such preferred kinetic properties could be represented by preferred or exclusive substrate specificities for the blood group A or B oligosaccharides, and low or no activity with simple monosaccharide derivatives such as monosaccharide-pNP substrates. Preferred kinetic properties could also be represented by a particularly low $K_m$ for relevant substrates. Further preferred kinetic properties consist of neutral pH optimum of reactions with relevant blood group active substrates, and other reaction conditions that are compatible with the integrity and functions of red cells. Other preferred properties of the enzyme such as size, charge, solubility, and other physico-chemical properties may also relate to performance in enzymatic conversion of red cells.

Novel α-galactosidases and α-N-acetylgalactosaminidases with improved kinetic properties were identified from various bacterial strains in the present invention as described in Examples 2, 3 and 4. The α-N-acetylgalactosaminidase (New England Biolabs) described in Example 4 represents one example of such an α-N-acetylgalactosaminidase and it was available in recombinant form of sufficient purity to test our hypothesis that enzymes with the above mentioned preferred characteristics would exhibit superior performance in red cell conversions.

Shown in Table XIII is the performance of this α-N-acetylgalactosaminidase in red blood cell conversions at neutral pH. The α-N-acetylgalactosaminidase was capable of completely converting both $A_1$ and $A_2$ red blood cells to cells typing as O as defined by routine blood bank typing protocols.

TABLE XIII

Conversion of $A_1$ and $A_2$ red blood cells with NEB α-N-acetylgalactosaminidase

| | Pre Enzyme Treatment | | | Post Enzyme Treatment | | | |
| --- | --- | --- | --- | --- | --- | --- | --- |
| | Ortho Anti-A | Dolichos biflorus | Ulex europaeus | Ortho Anti-A | Gamma Anti-A | Dolichos biflorus | Ulex europaeus |
| A1 Donor #1 | 4+ | 4+ | 0 | 0 | 0 | 0 | 4+ |
| A1 Donor #2 | 4+ | 4+ | 0 | 0 | 0 | 0 | 4+ |
| A1 Donor #3 | 4+ | 4+ | 0 | 0 | 0 | 0 | 4+ |
| A2 Donor #1 | 4+ | 0 | 3+ | 0 | 0 | 0 | 4+ |

TABLE XIII-continued

Conversion of $A_1$ and $A_2$ red blood cells with NEB α-N-acetylgalactosaminidase

| | Pre Enzyme Treatment | | | Post Enzyme Treatment | | | |
|---|---|---|---|---|---|---|---|
| | Ortho Anti-A | Dolichos biflorus | Ulex europaeus | Ortho Anti-A | Gamma Anti-A | Dolichos biflorus | Ulex europaeus |
| A2 Donor #2 | 4+ | 0 | 3+ | 0 | 0 | 0 | 4+ |
| A2 Donor #3 | 4+ | 0 | 2+ | 0 | 0 | 0 | 4+ |
| A2 Donor #4 | 4+ | 0 | 3+ | 0 | 0 | 0 | 4+ |
| A2 Donor #5 | 4+ | 0 | 2+ | 0 | 0 | 0 | 4+ |
| A2 Donor #6 | 4+ | 0 | 3+ | 0 | 0 | 0 | 4+ |

Protocol: Leuko-reduced red blood cells (Oklahoma Blood Institute) or red cells collected from volunteers (ACD), were washed once in 0.9% saline and resuspended in the conversion buffer to 30% hematocrit. Cells were treated with 10 to 20 mU/ml (One unit is defined as the amount of enzyme that hydrolyses 1 μmol of A tetrasaccharide AMC in 1 min using the standard reaction conditions described elsewhere) α-N-acetylgalactosaminidase (New England Biolabs) and incubated at 25° C. for 60 min with mixing. Treated cells were washed once with 0.9% saline, resuspended to 3-5% in saline, and typed as described above.

Red cells of both $A_1$ and $A_2$ subtypes treated with 10-20 mU α-N-acetylgalactosaminidase at neutral pH were totally unreactive with the anti-A typing reagents in direct agglutination assays. Instead enzyme treated A cells became equally reactive as control O cells with the lectin *Ulex Europaeus*, which is generally used as an anti-H reagent. The reactivity with Dolichus Biflorus which is generally used as an anti-$A_1$ reagent was destroyed within the first minutes of the treatment (not shown).

The cross-match analysis of α-N-acetylgalactosaminidase treated cells shown in Table XIV confirmed that both $A_1$ and $A_2$ enzyme converted cells behaved as O control cells.

TABLE XIV

Cross-match analysis (IS, immediate spin) of converted $A_1$ and $A_2$ red blood cells with NEB α-N-acetylgalactosaminidase
IS of Post Enzyme Treatment of Red cells

| | $A_1$ Donor #1 | $A_1$ Donor #2 | $A_1$ Donor #3 | $A_2$ Donor #1 | $A_2$ Donor #2 | $A_2$ Donor #3 | O Donor #1 |
|---|---|---|---|---|---|---|---|
| Plasma Saline control | 0 | 0 | 0 | 0 | 0 | 0 | 0 |
| $A_1$ plasma (n = 2) | 0 | 0 | 0 | 0 | 0 | 0 | 0 |
| $A_2$ plasma (n = 2) | 0 | 0 | 0 | 0 | 0 | 0 | 0 |
| O plasma (n = 7) | 0 | 0 | 0 | 0 | 0 | 0 | 0 |

This result shows that O and B individuals, who have variable titers of antibodies directed against blood group A antigens of A red cells, do not recognize these when the immunodominant αGalNAc residue is sufficiently removed. As described in the Background of the Invention and further illustrated in Table I, this result indicates that the minor amounts of glycosphingolipids containing the repetitive blood group A structure in agreement with our analysis in Example 4 is fully converted to the H associated A structure (Table I, structure 21). Furthermore, it indicates that this H associated A structure is perceived as a normal H antigen by the immune system. This is in accordance with our previous studies of the immunogenicity of this glycolipid antigen in mice (Clausen et al., *J Biol. Chem.* 261(3): 1380-7, 1986, Clausen et al., *Biol. Chem.* 261(3): 1388-92, 1986). The finding that enzymatic digestion with a single α-N-acetylgalactosaminidase enzyme renders $A_1$ as well as $A_2$ red cells non-reactive with anti-A typing reagents and plasma of group O and B individuals is novel and a major advancement in developing a commercially viable technology for providing universally acceptable enzyme converted O cells. While enzyme converted B cells chemically are predicted to be identical to O cells, enzyme converted A cells will phenotype as O but have two different types of H antigens. The majority of these two being the H type 2 structure (Table I, structure 18) found on O cells, but also a minor amount of H glycolipids with an internal structure consisting of a masked A trisaccharide is present (Table I, structure 21). Single enzyme α-N-acetylgalactosaminidase converted A cells are hence distinct from O cells and any red cells previously prepared and used in transfusion medicine, however, they are expected to function identical to O cells.

Detailed studies of the parameters of enzyme conversion of red cells with the *E. coli* expressed α-N-acetylgalactosaminidase were carried out for optimization. While pH influenced the activity of the enzyme activity with the A tetrasaccharide AMC substrate, none of the parameters tested and described below influenced this activity significantly.

Figure 11:
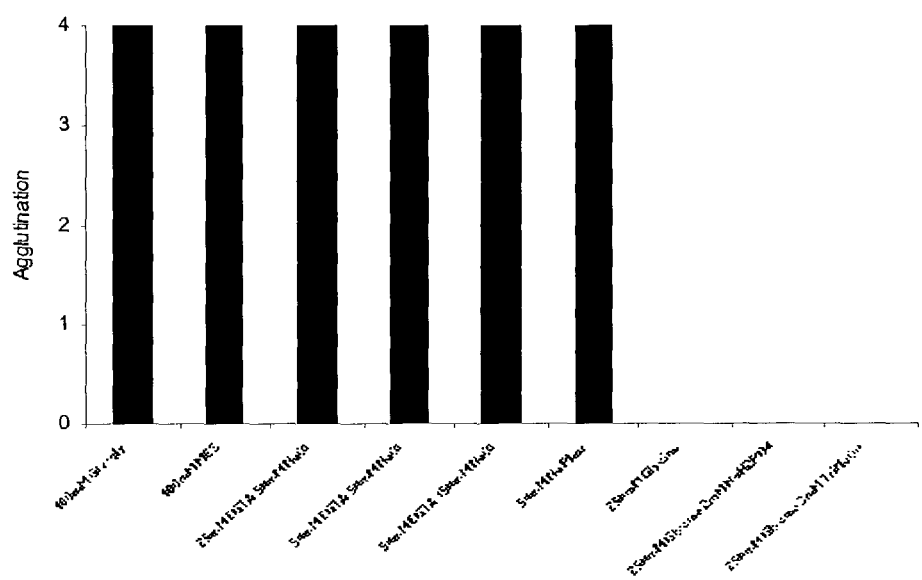
FIG. 11 illustrates the influence of buffer system on enzymatic conversion of $A_2$ cells using E. coli expressed α-N-acetylgalactosaminidase. Washed $A_2$ red cells were incubated with 5-20 mU/ml α-N-acetylgalactosaminidase in the designated buffers at 25° C. (30% cell suspension), and conversion evaluated at 30 and 60 min by agglutination with Ortho anti-A.

Buffer System:

As shown in FIG. 11, the optimal buffer system appeared to be 250 mM glycine. Reactions in NaP and PCI buffers, which are generally used for enzymatic conversion of B cells, did not produce significant conversion.

Figure 12:
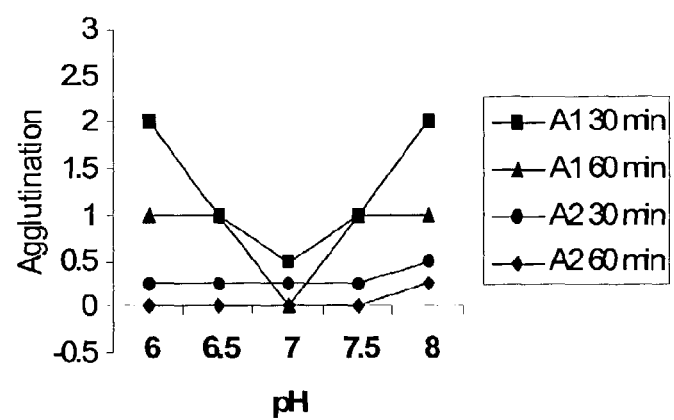
FIG. 12 illustrates the influence of pH using 250 mM glycine buffer on enzymatic conversion of $A_1$ and $A_2$ cells using E. coli expressed α-N-acetylgalactosaminidase. Washed red cells were incubated with 7.5 mU/ml α-N-acetylgalactosaminidase in 250 mM Glycine buffer pH 6.0 to 8.0 at 25° C. (30% cell suspension), and conversion evaluated at 30 and 60 min by agglutination with Ortho anti-A.

Glycine Buffer pH:

The *E. coli* expressed α-N-acetylgalactosaminidase was found in Example 4 to have a broad pH optimum around neutral pH. Analysis of the pH optimum in enzymatic conversion of $A_1$ and $A_2$ cells revealed a more defined optimum at pH 7 (FIG. 12). Conversion of the weak $A_2$ cells was achieved at a broader range of pH 6-8 with 7.5 mU/ml enzyme, but if less enzyme was used the optimum was at pH 7 (not shown).

Figure 13:
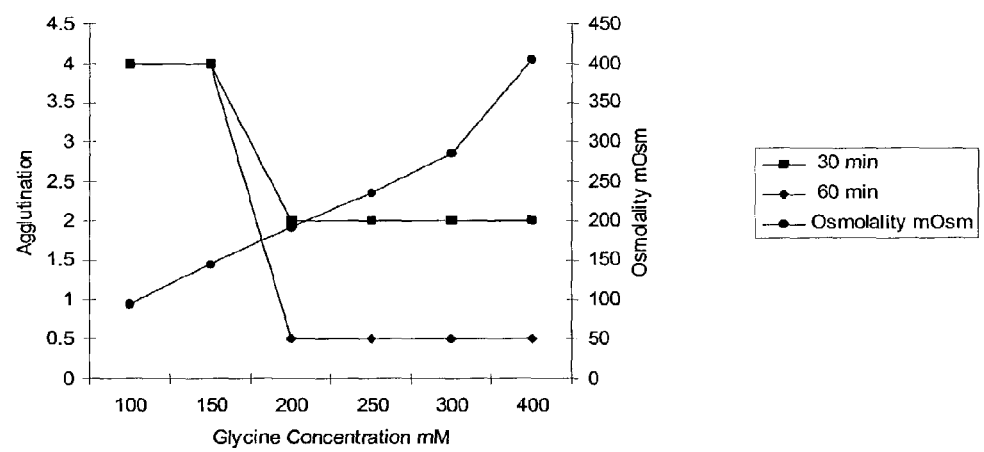
FIG. 13 illustrates the influence of glycine buffer concentration on enzymatic conversion of $A_1$ cells using E. coli expressed α-N-acetylgalactosaminidase. Washed red cells were incubated with 7.5 mU/ml α-N-acetylgalactosaminidase in 100-400 mM Glycine buffer pH 7.0 at 25° C. (30% cell suspension), and conversion evaluated at 30 and 60 min by agglutination with Ortho anti-A.

Glycine Buffer Molarity:

The concentration of glycine was found to be an important parameter for enzyme conversion of group A cells with the *E. coli* expressed α-N-acetylgalactosaminidase (FIG. 13). Optimal conversion was achieved at 250-300 mM.

Figure 14:
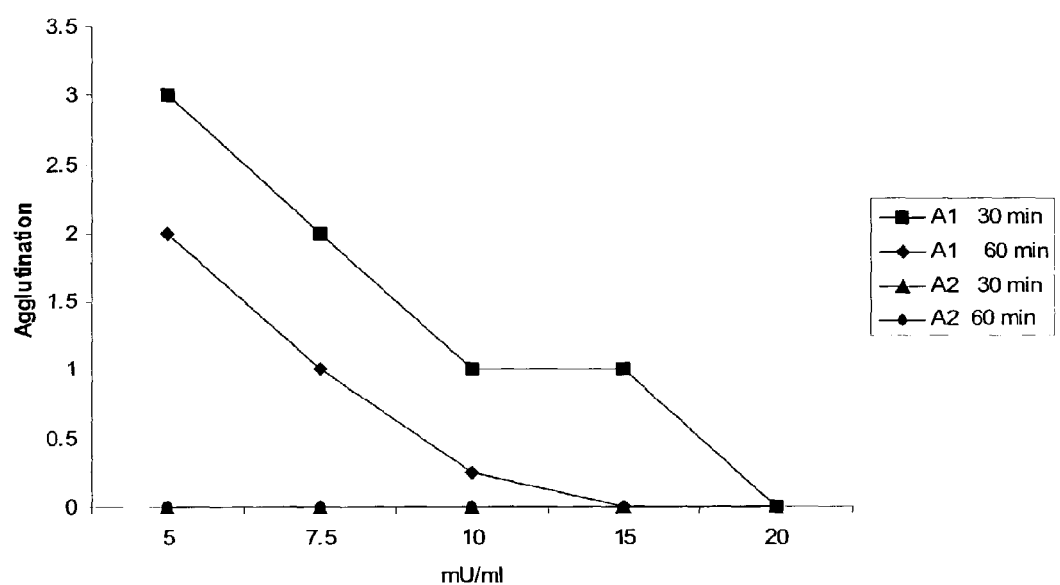
FIG. 14 illustrates the influence of concentration of E. coli expressed α-N-acetylgalactosaminidase enzymatic conversion of $A_1$ and $A_2$ cells. Washed red cells were incubated with 5-50 mU/ml α-N-acetylgalactosaminidase in 250 mM Glycine pH 7.0 at 25° C. (30% cell suspension), and conversion evaluated at 30 and 60 min by agglutination with Ortho anti-A.

Enzyme Concentration:

FIG. 14 illustrates titration of the *E. coli* expressed α-N-acetylgalactosaminidase from 5-50 mU/ml with $A_1$ and $A_2$ cells. In agreement with $A_1$ having more A antigenic Epitopes than $A_2$, more enzyme is required to convert $A_1$ cells. Titration of enzyme on $A_2$ cells from 1-10 mU revealed that 3 mU/ml was required to fully convert with the used conditions (not shown).

Figure 15:
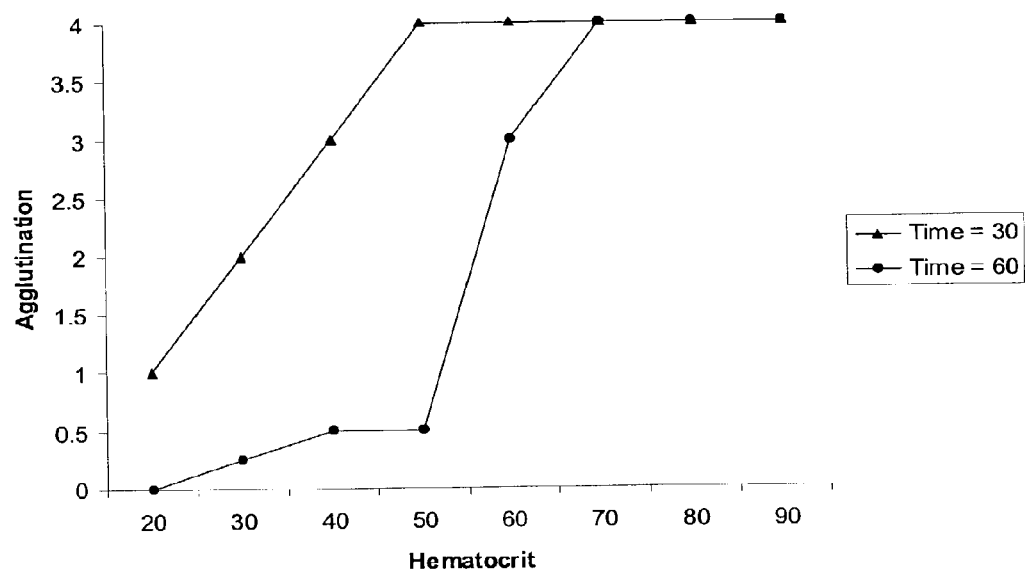
FIG. 15 illustrates the influence of concentration of cells (hematocrit) on enzymatic conversion of $A_1$ cells using E. coli expressed α-N-acetylgalactosaminidase. Washed red cells were incubated with 20 mU/ml α-N-acetylgalactosaminidase in 250 mM Glycine pH 7.0 at varying concentrations 20-90% at 25° C., and conversion evaluated at 30 and 60 min by agglutination with Ortho anti-A.

Influence of Concentration of Cells (Hematocrit) During Treatment:

Treatment of $A_1$ cells at concentrations from 20-90% with constant amount of enzyme (20 mU) showed that conversion efficiency decreased with increasing cell concentration (FIG. 15). At higher concentrations of enzyme, conversion occurred faster, but conversion efficiency at cell concentrations above 50% did not improve proportionally suggestion that optimal conversion conditions are 20-50%.

Figure 16:
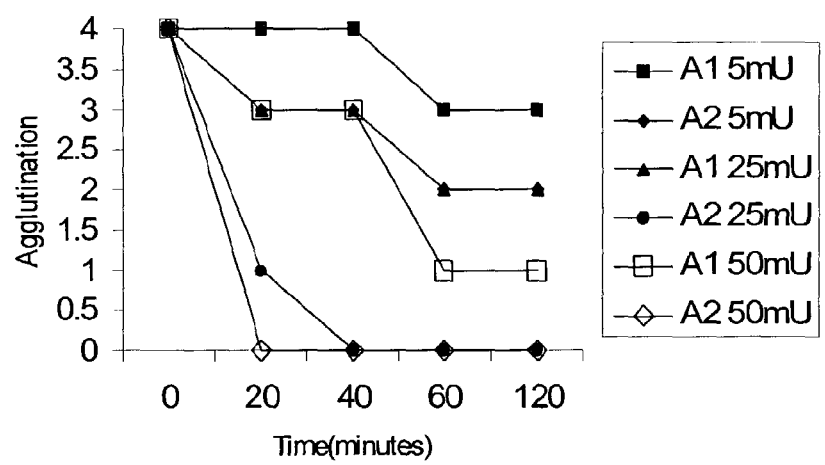
FIG. 16 illustrates the influence of reaction time on enzymatic conversion of $A_1$ and $A_2$ cells using E. coli expressed α-N-acetylgalactosaminidase. Washed red cells were incubated with 5-50 mU/ml α-N-acetylgalactosaminidase in 150 mM Glycine pH 7.0 at 25° C. (30% cell suspension), and conversion evaluated at 20, 40, 60, and 120 min by agglutination with Ortho anti-A.

Influence of Treatment Time:

FIG. 16 illustrates that conversion is proportional with amount of enzyme and time.

Influence of Temperature:

The activity of the *E. coli* expressed α-N-acetylgalactosaminidase with saccharide derivative at the temperature interval 20-40° C. was found to be similar, and the performance of the enzyme in group A cell conversion as illustrated in FIG. 17 confirmed this.

These results clearly demonstrate that one α-N-acetylgalactosaminidase, exemplified by the *E. coli* expressed α-N-acetylgalactosaminidase used in this example having the preferred unique kinetic properties defined in this invention, exhibits improved performance in enzymatic conversion of group A cells. Conversion of group $A_1$ cells, which has not previously been achieved, was achieved with the preferred enzyme at neutral pH and at enzyme protein concentrations much below those previously used for converting $A_2$ and B cells. The amount of enzyme used (10-20 mU/ml equivalent to 30-60 μg/ml) for conversion of 30% suspension of cells (hematocrit), is lower than any amount of enzyme reported in the prior art to enzymatically convert A and B red cells.

$A_1$ and $A_2$ cells treated with an exo-N-acetylgalactosaminidase as the *E. coli* expressed α-N-acetylgalactosaminidase used in this example capable of cleaving GalNAc from all blood group A structures will expose the classical H type 2 chain antigens (structure 18, Table 1) as found on blood group O cells, but it will also leave a small amount of glycolipids with the A associated H structure (structure 21, Table 1). Studies with monoclonal antibodies specifically reactive with H type 2 (BE2) and H type 3 (HH14, MBr-1) (see Clausen et al., *J Biol. Chem.* 261(3): 1380-7, 1986) revealed as expected that exo-N-acetylgalactosaminidase treated A cells reacted strongly with BE2 and weaker with HH14 and MBr-1 (not shown). Since none of the anti-A antibodies including those used for routine blood typing reacted with treated cells (Table XIII) the A-associated H glycolipid structure is not recognized as an A antigen. This was further confirmed by cross-match analysis (Table XIV). This is in agreement with the fact that anti-H type 3 chain antibodies fails to distinguish between the above glycolipid and the structures named H-Globo and mucin-type H (structures 22 and 21, respectively, Table 1) (Clausen et al., *J Biol. Chem.* 261(3): 1380-7, 1986). Thus, although exo-N-acetylgalactosaminidase treated A cells behave as O cells phenotypically, they differ structurally from O cells by having minor amounts of the unique H glycolipid antigens. The group A enzyme converted cells typing as group O therefore constitute a novel entity which is highly useful as a universal transfusable type of blood.

The novel *Streptomyces* enzymes defined in Example 3 have properties 30 fold or better compared to the α-N-acetylgalactosaminidase used in this example, and this and other enzymes with similar properties are predicted to perform correspondingly better in enzymatic red cell conversions.

Equivalents

Those skilled in the art will recognize, or be able to ascertain using no more than routine experimentation, numerous equivalents to the specific procedures described herein. Such equivalents are considered to be within the scope of the present invention and are covered by the following claims. Various substitutions, alterations, and modifications may be made to the invention without departing from the spirit and scope of the invention as defined by the claims. Other aspects, advantages, and modifications are within the scope of the invention. The contents of all references, URLs, issued patents, and published patent applications cited throughout this application are hereby incorporated by reference. The appropriate components, processes, and methods of those patents, applications and other documents may be selected for the present invention and embodiments thereof.

What is claimed is:

1. An isolated *Streptomyces griseoplanus* cell of a *Streptomyces griseoplanus* cell line deposited with ATCC under Deposit No. PTA-4077.

2. The isolated *Streptomyces griseoplanus* cell of claim 1 that expresses an α-galactosidase for removing immunodominant α-galactose monosaccharides from blood group B or AB reactive cells of blood products, wherein the α-galactosidase is active at said removing at neutral pH.

3. The isolated *Streptomyces griseoplanus* cell of claim 2, wherein said α-galactosidase has no detectable activity with an α-Gal p-nitrophenyl monosaccharide derivative.

4. The isolated *Streptomyces griseoplanus* cell of claim 2, wherein said α-galactosidase has no detectable activity with a $P_1$ antigen.

* * * * *